United States Patent [19]

Chan

[11] Patent Number: 5,562,687

[45] Date of Patent: Oct. 8, 1996

[54] SURGICAL REPAIR KIT AND ITS METHOD OF USE

[75] Inventor: Kwan-Ho Chan, Joplin, Mo.

[73] Assignee: Mitek Surgical Products, Inc., Westwood, Mass.

[21] Appl. No.: 90,651

[22] Filed: Jul. 12, 1993

[51] Int. Cl.⁶ ..................................... A61B 17/00
[52] U.S. Cl. ......................... 606/148; 606/139; 604/272; 604/280; 72/367
[58] Field of Search ..................... 606/139, 144, 606/148, 103, 222, 223; 289/117; 604/264, 272, 274, 164, 170, 280; 72/367, 369

[56] References Cited

U.S. PATENT DOCUMENTS

| | | | |
|---|---|---|---|
| 2,286,578 | 6/1942 | Sauter | 606/144 |
| 2,406,838 | 9/1946 | Kepler | 72/369 |
| 2,455,833 | 12/1948 | Trombetta | 606/139 |
| 3,472,231 | 10/1969 | Nieble | 606/167 |
| 4,177,813 | 12/1979 | Miller et al. | 606/139 |
| 4,545,374 | 10/1985 | Jacobson | 604/164 |
| 4,864,762 | 9/1989 | Cox | 289/17 |
| 4,923,461 | 5/1990 | Caspari et al. | 606/148 |
| 5,236,434 | 8/1993 | Callicrate | 606/139 |
| 5,263,936 | 11/1993 | Yurino | 604/158 |
| 5,342,369 | 8/1994 | Harryman, II | 606/96 |
| 5,364,409 | 11/1994 | Kuwabara et al. | 606/148 |
| 5,382,258 | 1/1995 | Chow | 606/148 |

FOREIGN PATENT DOCUMENTS

| | | | |
|---|---|---|---|
| 453256 | 1/1929 | Germany | 606/148 |
| 0649416 | 2/1979 | U.S.S.R. | 606/139 |
| 1192881 | 11/1985 | U.S.S.R. | 72/369 |

*Primary Examiner*—Stephen C. Pellegrino
*Assistant Examiner*—Jeffrey A. Schmidt
*Attorney, Agent, or Firm*—Pandiscio & Pandiscio

[57] ABSTRACT

A suture passer comprises a longitudinally extending hollow cannula having a central passage slidingly receivable of a surgical suture; a manually graspable handle connected to the hollow cannula for manipulation thereof, the handle having an upper surface; first guide means, connected to the upper surface of the handle, proximate a proximal end of the handle for releasably, guidingly, holding the surgical suture; second guide means, connected to the upper surface of the handle, distal to the first guide means, for releasably, guidingly, holding the surgical suture. The suture passer can be provided in a kit, for use in the suturing of internal tissue, along with a cannula bender, various hollow surgical needles and surgical suture material. The suture passer finds particular use in the suturing of internal tissues which are at least partially accessible through a body cavity, e.g., arthroscopic surgery.

18 Claims, 27 Drawing Sheets

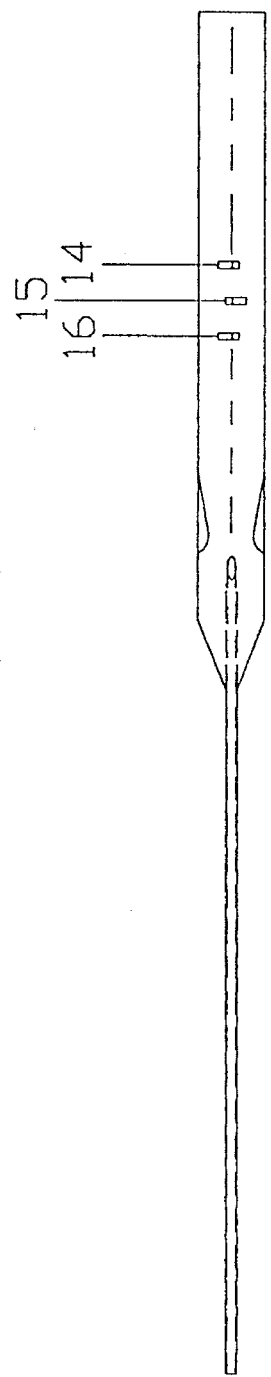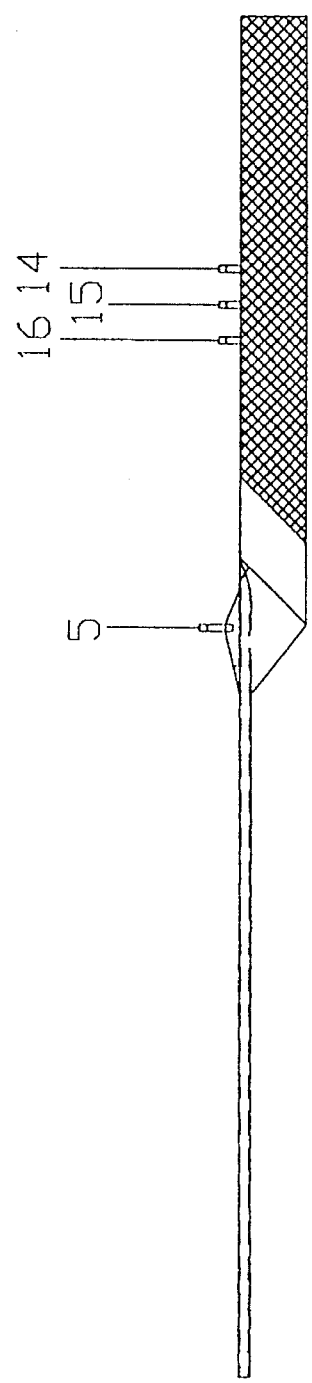
FIG. 7B
FIG. 7A

EPIDURAL NEEDLE

18

SPINAL NEEDLE

17

SURGICAL REPAIR KIT AND ITS METHOD OF USE

FIELD OF THE INVENTION

The present invention relates to medical devices for performing surgery and a surgical repair kit containing the same. More particularly, the present invention is directed to a surgical repair kit useful for performing arthroscopic meniscal repairs.

BACKGROUND OF THE INVENTION

Menisci are tough rubbery "C" shaped cartilage cushions that are attached by ligaments to the top (plateau) of the tibia. They prevent the surfaces of the tibia and femur from grinding against each other and act as the shock absorbers in the knee.

Meniscal tears are a common problem in the United States, menisci are also located in the shoulder, the most common meniscus injury occurs in the knee. There are two menisci in each knee. Each year, tens of thousands of people suffer meniscal tears, particularly in or at the site of one or both knees. If these tears are not repaired, there may be a progressive deterioration of the cartilage, leading to the painful rubbing and wearing of bones which had previously been covered by cartilage. This, in turn, leads to inflammatory synovitis, arthritis and other debilitating ailments. Consequently there are at least 30,000 to 40,000 meniscal excisions or repairs to the shoulder and the knee performed each year.

Men and women between the ages of 18 and 45 experience the majority of meniscal tears, usually during athletic activity, such as when twisting, cutting, pivoting, decelerating or when being tackled. When torn, the meniscus may have a longitudinal, horizontal, or radial ("parrot beak") tear.

The damaged meniscus may be diagnosed with the assistance or use of magnetic resonance imaging (MRI) and/or an arthroscopic examination. Arthroscopy enables a surgeon to look into the joint using a miniature video camera. In many cases, torn fragments of the meniscus are removed arthroscopically. In other cases, a small tear at the periphery of the meniscus with a very swollen knee joint may be treated by draining the joint, temporarily restricting the use of the knee, and slowly having the patient begin rehabilitative exercises.

However, in other cases, the tears in the meniscus do require surgical repair, normally by sewing the torn sections of the meniscus together. The use of the arthroscope greatly aids in the surgical repair of the meniscus by allowing the surgeon to better visualize the small areas between which the torn meniscus lies. The arthroscope enables the surgeon to visualize the interior of the joint and to perform surgery through small puncture holes without having to open the joint as has been done in the past.

A number of surgical tools have been developed to assist in suturing, and in particular the suturing of the meniscus.

U.S. Pat. No. 2,808,055 (Thayer) discloses a surgical stitching instrument which accommodates a bobbin of suture material and include means to feed the suture material to a needle. A slidable thread moving member is provided for advancing the suture material through the needle.

U.S. Pat. No. 3,476,114 (Shannon, et al.) discloses a ligating implement comprising an elongated instrument through which a ligature passes to form a loop at one end with a disc. The disc provides a means whereby the loop may be drawn tight above a severed vessel or the like.

U.S. Pat. No. 3,476,115 (Graeff, et al.) discloses a ligating implement as in Shannon, et al., and includes severing means to prevent overstressing of the locking disc during tightening of the noose.

U.S. Pat. No. 4,493,323 (Albright, et al.) discloses a suturing device and a method for its use in arthroscopic surgery. The suturing device comprises an elongated tube and plunger which are used to hold and advance a pair of needles united by a length of suture material.

U.S. Pat. No. 4,641,652 (Hutterer, et al.) discloses an applicator for tying sewing threads which comprises a helical tubular coil connected to a shaft having an axial passage. A catcher loop is extendable through the shaft to catch a sewing thread inserted manually into the coil passage.

U.S. Pat. No. 4,935,027 (Yoon) discloses surgical instruments and methods for affecting suturing of tissue controlled from a position remote from the suture site. The invention provides for the continuous feeding of suture material through opposed forcep jaw members between which the tissue segments are interposed.

U.S. Pat. No. 5,112,308 (Olsen, et al.) discloses a medical device for and a method of endoscopic surgery. The device includes a dilator having a tapered end and a central passage which accommodates a guide wire for directing the dilator. This device does not include any means whereby the guide wire may be secured to the dilator or otherwise manipulated in conjunction therewith.

U.S. Pat. No. 4,779,616 (Johnson) discloses a method for snagging an end of a surgical suture during arthroscopic surgery, comprising deploying a distal end of a cylindrical cannula adjacent to the end of the suture within the body and passing a resilient loop through the cannula to snag the suture.

U.S. Pat. Nos. 4,890,615, 4,923,461 and 4,957,498 (Caspari, et al.) disclose a suturing instrument and method of use in arthroscopic surgery. The suturing instrument includes a hollow needle for penetrating tissue to be sutured within the body while the tissue is clamped between relatively moveable jaws and a suture feed mechanism for feeding suture material through the hollow needle. The jaws can be opened and the suturing instrument withdrawn from the body, pulling the free end segment of the suture material with the instrument.

SUMMARY OF THE INVENTION

It is an object of the present invention to provide a surgical repair kit. In particular, it is an object of the present invention to provide a surgical repair kit which is particularly suited for the repair of torn menisci.

It is another object of the present invention to provide a suture passer having means for positioning of the suture.

It is another object of the present invention to provide a parallel needle guide to allow for an easier and more successful placement of a second needle in close proximity to the first needle that has been previously inserted in the area of a tissue tear.

While the present invention is primarily concerned with the repair of torn menisci, the repair kit, the parallel needle guide, and the suture passer may be used in other surgical procedures, e.g. for suturing internal tissue at least partially accessible through a body cavity.

The suture passer of the invention comprises a longitudinally extending hollow cannula having a central passage slidingly receivable of a surgical suture and a manually graspable handle connected to the hollow cannula for manipulation thereof. The suture passer has a first guide means connected to an upper surface of the handle, proximate to a proximate end of the handle for releasably, guidingly holding the surgical suture, and a second guide means connected to the upper surface of the handle, distal to the first guide means for releasably, guidingly holding the surgical suture.

In one embodiment of the invention, the hollow cannula is connected to the upper surface of the handle and the hollow cannula terminates at a rearward opening between the first and second guide means.

In another embodiment of the invention, the hollow cannula is received within a bore formed in the handle, with the bore terminating at an opening in the upper surface of the handle between the first and second guide means.

The guide means may be loops which are either parallel or transverse to the longitudinally extending hollow cannula. In an alternative embodiment, the second guide means may consist of a plurality of bent fingers lying in parallel planes.

The guide means serve as means about which the suture is passed so it may be manipulated longitudinally with respect to the cannula. The diameter of the central passage of the cannula is such that the tip of a spinal or similar needle into which the suture is directed may fit into the cannula and is large enough to allow the sliding passage of two surgical sutures (i.e. the two limbs of a single surgical suture). In the method of use, the suture passer is used in surgical manipulations, and in particular meniscal repairs or other arthroscopic procedures to direct a suture within a joint space with a greater degree of precision than available by current methods.

When the two limbs of a surgical suture are within the cannula, the guide means function to separate the two limbs. Separation of the limbs of the surgical suture allows independent manipulation of the suture limbs. Digital manipulation of the surgical suture between the proximal and distal guide means causes longitudinal passage of one limb of the surgical suture within the cannula, i.e. friction between the digit and the said suture will cause the said suture to slide along the top surface of the handle, into or out of the cannula, when manipulated digitally.

The surgical repair kit of the present invention comprises a suture passer, as previously described, at least two surgical needles of predetermined length and at least one stylet for each surgical needle. Preferably, the surgical repair kit includes three surgical needles, with one of the surgical needles having a length greater than that of the other needles.

In a preferred embodiment, the suture passer is provided with a metal cannula, and the surgical repair kit includes a cannula bender for bending the metal cannula in a desired manner. The cannula bender comprises a base and a pair of upwardly stepped symmetrical bolsters positioned on top of the base allowing the cannula to be bent to the right or to the left, each step of each bolster having a predetermined radius of curvature wherein the radius of curvature of each step is smaller than the radius of curvature of the step immediately below.

Additionally, the surgical repair kit of the present invention may further include a parallel needle guide for guiding the surgical needles for desired placement relative to each other. The parallel needle guide comprises at least three longitudinally extending, hollow tube-shaped units longitudinally adhered to each other, in a plane, parallel to one another, each of the tube-shaped units slidingly receivable of a surgical needle therethrough.

The present invention also provides methods for the suturing of internal tissue which is at least partially accessible through a body cavity. A first method comprises the steps of:

(A) providing at least one suture having a first limb and a second limb;

(B) providing a suture passer comprising a longitudinally extending hollow cannula having a distal opening, a proximal opening and a central passage slidingly receivable of a surgical suture;

(C) introducing the distal end of the cannula into a body cavity at least partially accessing internal tissue to be sutured;

(D) identifying a first insertion site for passing a first limb of a suture through the internal tissue to be sutured;

(E) inserting a first hollow needle through the first insertion site, the hollow needle extending from outside the body through the first insertion site into the body cavity;

(F) identifying a second insertion site for passing a second limb of the suture through the internal tissue to be sutured;

(G) inserting a second hollow needle through the second insertion site, the hollow needle extending from outside the body through the second insertion site into the body cavity;

(H) passing the second limb of the suture through the first hollow needle into the distal opening of the cannula until it exits the proximal opening of the cannula;

(I) feeding the second limb of the suture back into the cannula through the proximal opening;

(J) passing the second limb of the suture through the hollow cannula into the second hollow needle until it exits the needle external of the body;

(K) drawing the suture through the cannula into the body cavity;

(L) removing the first and second needles by drawing them outwardly of the body cavity;

(M) tying the limbs of the suture; and (N) repeating steps (D)–(M) until a surgically sufficient number of sutures have been tied.

A second method comprises the steps of:

(A) providing at least one suture having a first limb and a second limb;

(B) providing a suture passer comprising a longitudinally extending hollow cannula having a distal opening, a proximal opening and a central passage slidingly receivable of a surgical suture;

(C) loading the suture passer with a surgical suture such that an end of the first limb of the suture and an end of the second limb of the suture each protrude from the distal end of the cannula;

(D) introducing the distal end of the cannula into a body cavity at least partially accessing internal tissue to be sutured;

(E) identifying a first insertion site for passing the first limb of the suture through the internal tissue to be sutured;

(F) inserting a first hollow needle through the first insertion site, the hollow needle extending from outside the body through the first insertion site into the body cavity;

(G) identifying a second insertion site for passing a second limb of the suture through the internal tissue to be sutured;

(H) inserting a second hollow needle through the second insertion site, the hollow needle extending from outside of the body through the second insertion site into the body cavity;

(I) introducing the end of the first limb of the suture into the first hollow needle until it exits the first hollow needle outside the body;

(J) introducing the end of the second limb of the suture into the second hollow needle until it exits the second hollow needle outside the body;

(K) drawing the suture through the cannula into the body cavity;

(L) removing the first and second hollow needles by drawing them outwardly of the body cavity;

(M) tying the limbs of the suture; and (N) repeating steps (C)–(M) until a surgically sufficient number of sutures have been tied.

BRIEF DESCRIPTION OF THE DRAWINGS

FIG. 7A is a side view and FIG. 7B is a top view of another embodiment of the surgical suture passer.

DETAILED DESCRIPTION OF THE PREFERRED EMBODIMENTS

Figure 1:
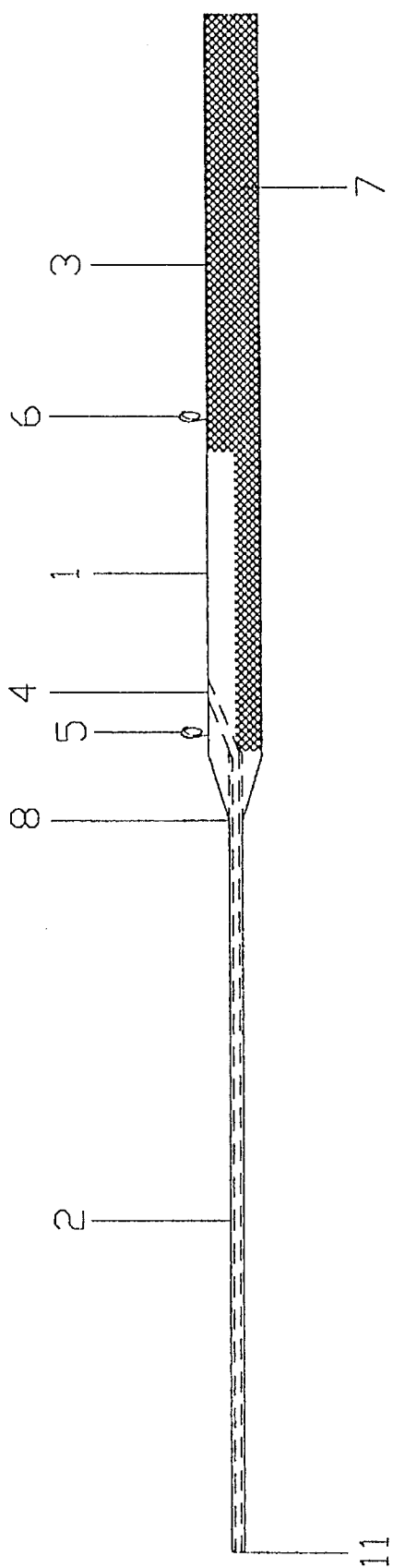
FIG. 1 is a side view of the suture passer.
Figure 2:
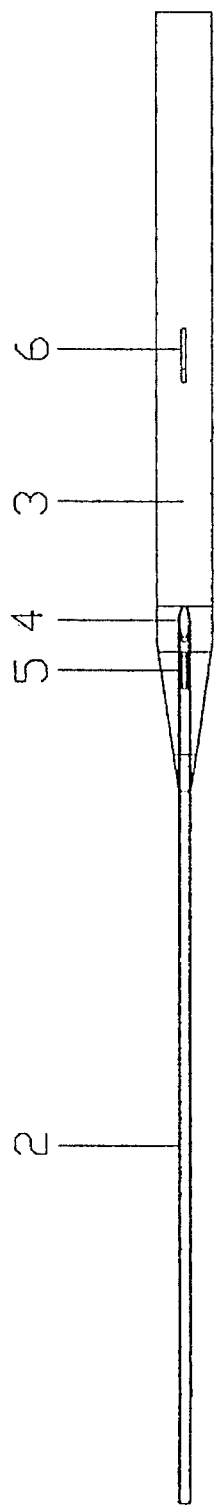
FIG. 2 is a top view of another embodiment of the suture passer.

FIGS. 1–7 illustrate the meniscal suture passer 1, used for the passage of a suture in a confined area of the body during surgery. The suture passer 1 comprises a longitudinally extending hollow cannula 2 having a central passage slidingly receivable of a surgical suture, and a manually graspable handle 3 connected to the hollow cannula 2 for manipulation thereof. A first guide means is connected to the upper surface of the handle 3 for releasably, guidingly holding the surgical suture. A second guide means for guidingly holding the suture, is also connected to the upper surface of the handle 3. The second guide means is distal to the first guide means. The suture passer 1 in FIGS. 1–6 comprises the cannula 2, a handle 3, a rearward opening 4 near the proximal end of the handle 3, a proximal loop 5, and a distal loop 6. The proximal loop 5 serves as the first guide means, and the distal loop 6 serves as the second guide means. Proximal loop 5 preferably comprises a single turn open wire loop having a first axis of rotation of the loop and distal loop 6 is preferably a 1½ pigtail open wire loop having a second axis of rotation of the loop. The loops are preferably parallel to one another. In one embodiment, the wire loops 5 and 6 are preferably perpendicular to the handle 3 with the first axis of rotation and the second axis of rotation are transverse to the longitudinally extending hollow cannula 2. In another embodiment, the axes of rotation of loops 5 and 6 are parallel to the longitudinally extending cannula 3. Near the proximal end of the handle there is an opening 4 which leads from the handle 3 to the cannula 2. The handle is preferably provided with gripping means and is preferably knurled 7, so that the surgeon has a better grip on the suture passer 1.

Figure 3:
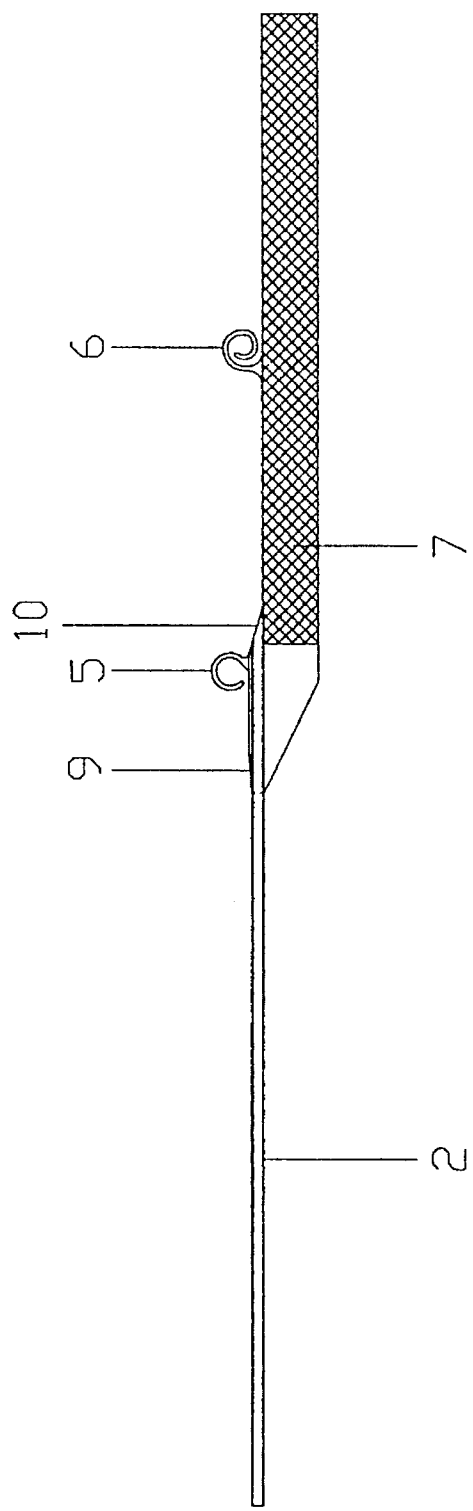
FIG. 3 is a side view of the suture passer of FIG. 2.
Figure 4:
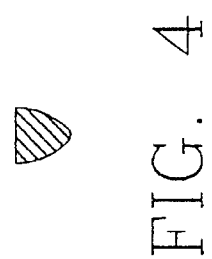
FIG. 4 is a frontal view of the handle of the embodiment of the surgical suture passer of FIG. 3.

The cannula 2 may be attached and enter through an opening at the concentric center 8 of the handle 3 as shown in FIG. 1. The hollow cannula 2 is received within a bore formed in the handle 3 with the bore terminating at the opening 4 in an upper surface 9 of the handle 3 intermediate the first and second guide means. In an alternative embodiment the cannula may be connected to the upper surface 9 of the handle 3, as shown in FIG. 3. In this embodiment of the invention, there is no opening into or through the handle 3. Instead, the hollow cannula 2 terminates at a rearward opening 10 between the first and second guide means directly on top of the handle 3. Additionally, in the embodiment of FIG. 1, the handle of the suture passer is rounded, whereas in the embodiment of FIGS. 3 and 4, the suture passer handle 3 is flattened on the side upon which the proximal end of the cannula 2 resides. Additionally, in the embodiment of FIG. 3, the proximal loop 5 resides on the cannula 2 just prior to the proximal opening 4 of the cannula 2.

The central passage of the cannula should have a diameter large enough to allow sliding passage of two surgical sutures therethrough. The distal opening 11 of the cannula should also have a diameter large enough to allow engagement with the tip of a spinal needle for the purpose of passage of the suture between the cannula and the needle.

In the embodiment of FIG. 1, the cannula 2 from its distal opening 11 to the point at which it enters the handle ranges in length from about 6.0 cm to about 20.0 cm, and more preferably 12.0 cm in length. The opening of the cannula 2 is preferably from about 0.08 cm to about 0.32 cm in width, and more preferably 0.16 cm in width. The wall of the cannula 2 is preferably from about 0.01 cm to about 0.05 cm in thickness, and more preferably, 0.0254 cm in thickness. The handle preferably has a width ranging from about 0.64 cm to about 1.28 cm, and more preferably 0.96 cm in width.

Figure 5:
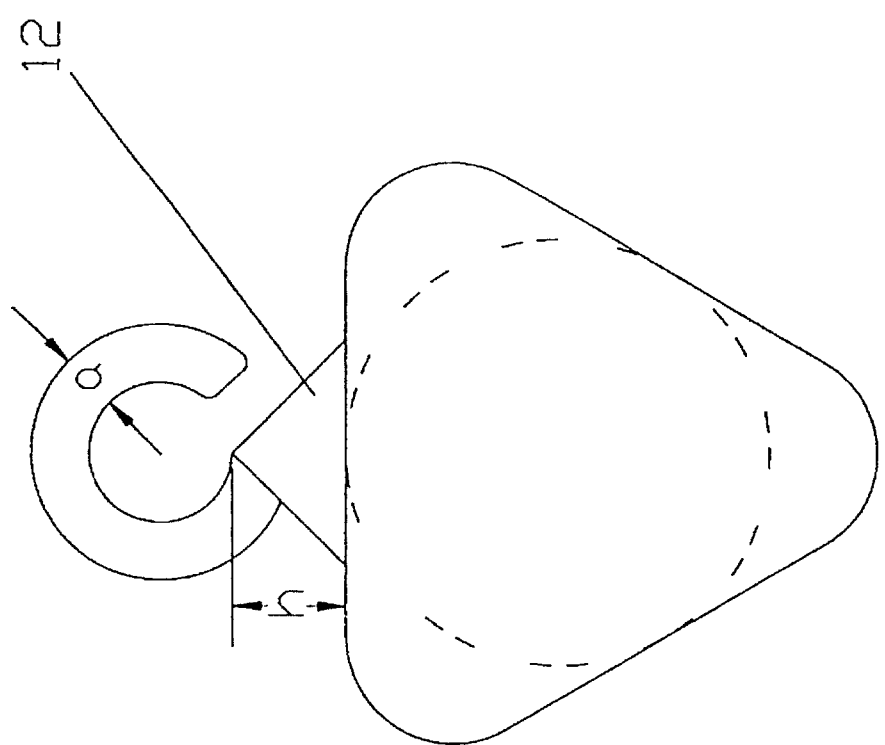
FIG. 5 is a cross section of the handle of the surgical suture passer.

The wire of the wire loops as shown in FIG. 5 ranges from about 0.10 to about 0.14 cm in diameter "a" and is preferably attached to the handle by a mounting structure 12 about 0.1 to about 0.4 cm in height "h."

Figure 6:
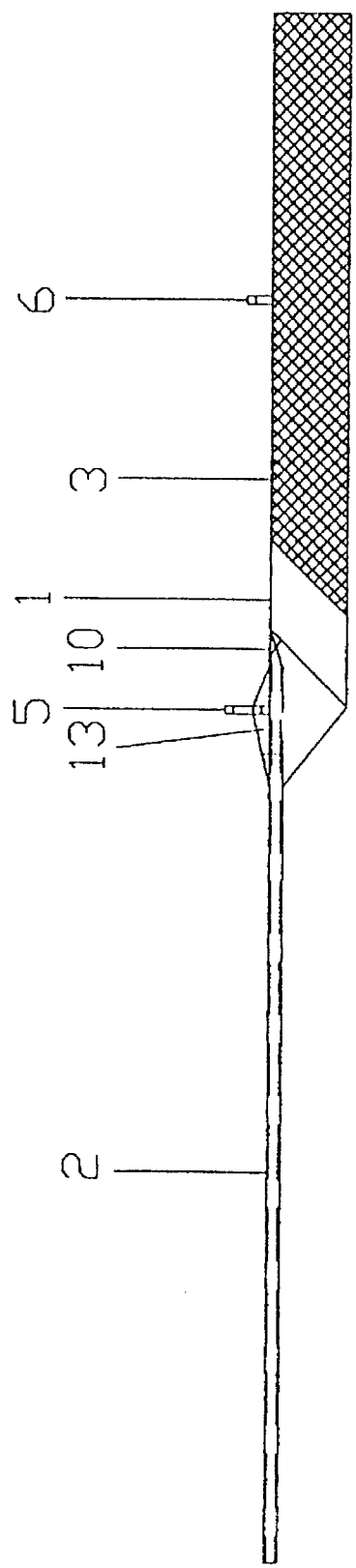
FIG. 6 is a side view of another embodiment of the surgical suture passer.

In the embodiment of the invention illustrated in FIG. 6, the suture passer 1 is similar to the invention illustrated in FIG. 3; however, the cannula 2 is flush with the flattened surface of the handle 3 bearing the wire loops 5 and 6. A segmented piece 13 upon which the proximal loop 5 resides attaches the cannula 2 to the handle 3. The proximal opening be of the cannula opens on the proximal side of the segmented piece 13.

In all of the embodiments of the meniscus suture passer 1, the distal loop 6 may be fitted anywhere along the length of the handle. However, it is preferable that the distal loop 6 be fitted about halfway between the ends of the handle of the suture passer.

In yet another embodiment of the invention, shown in FIG. 7, first guide means comprises a single turn open loop 5 lying in a first plane, with the first plane disposed perpendicularly to the longitudinally extending hollow cannula, and a second guide means comprising a plurality of bent fingers lying in parallel planes. The planes are parallel to each other and are perpendicular to the longitudinally extending hollow cannula. The bent fingers may be alternately bent in opposite directions. As shown in FIGS. 7A and 7B, the second guide means may have 3 bent fingers 14, 15, 16.

The suture passer 1 may be made out of either plastic or metal, and a combination thereof, with the handle, loops, or cannula being plastic, metal or any combination thereof. The cannula of the meniscal suture passer may be semi-rigid. The cannula should be rigid enough to stabilize the inner tear of the meniscus during the insertion of the epidural needle. Additionally, if made of plastic, the cannula should be malleable enough that it can be bent by hand without the need of a special bender. After the cannula is bent it should not spring back. Because of its malleable characteristics, the plastic material is less likely to damage the articular surface. If the suture passer is entirely made out of plastic, the entire suture passer device can be injection molded as a single unit. If the handle is made out of plastic material, the loop or the finger projections may be molded as an integral part of the handle.

If the suture passer is made out of metal, however, the loops may be screwed, riveted, or soldered onto the handle of the suture passer.

Frequently, surgical instruments and suturing devices must be adaptable to the environment or conditions in which they are being used. More specifically, because of the location of the menisci in the shoulder and in the knee, or because there is limited space in that part of the body being repaired for the placement of surgical tools, especially during suturing, it is frequently advisable to adjust the shape of the cannula of the suture passer or to bend the needles being used during suturing to allow for the positioning of the instruments into or through the surgical incision to allow for maximum visibility on the part of the operating team and to avoid crowding of the incision area which would hinder the operating team.

Preferably included in the surgical repair kit when the cannula is made out of metal is a cannula bender. The cannula bender may be used to bend the cannula without kinking the cannula.

Figure 12:
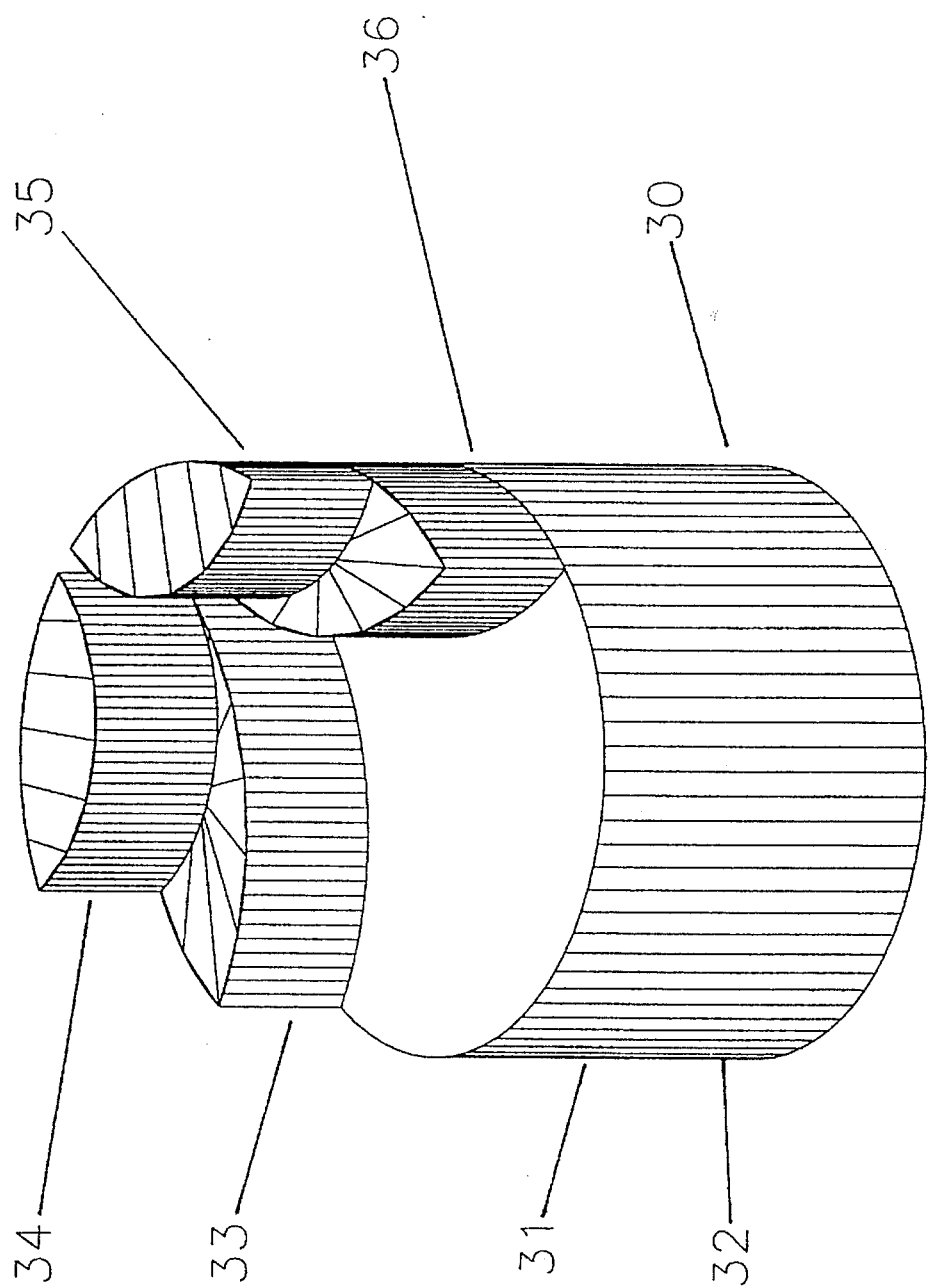
FIG. 12 is a frontal view of a cannula bender.
Figure 13:
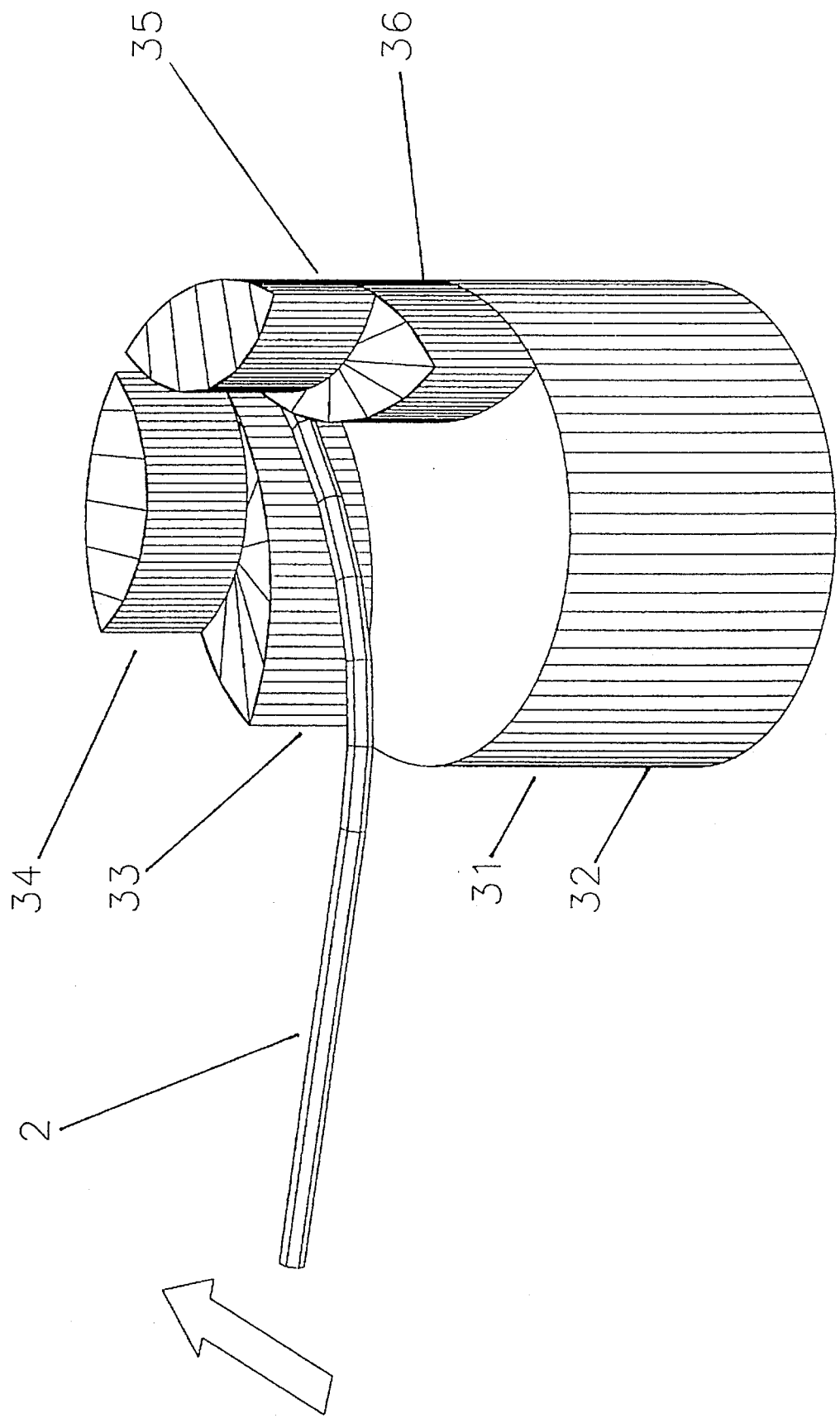
FIG. 13 is a frontal view illustrating the use of the cannula bender.

The cannula bender 30 shown in FIGS. 12 and 13 is designed to bend a cannula to a desired curvature. It is different from the existing tube or cannula benders in that it allows the cannula to be bent to various radii of curvature. The cannula bender 30 can also bend the cannula in more than one plane.

The cannula bender 30 consists of a base 31 with an approximate diameter of from about 1.25 cm to about 8 cm, with a preferred diameter of about 3.8 cm. The base which is preferably curved, circular, or oval in shape, serves as a handle by which the cannula bender is grasped. The base 31 may be knurled or striated to provide for a better grip.

There are symmetrical curved bolsters having steps 33, 34, 35, and 36 on top of the base. The stepped configuration provides the higher steps 34, 35 with a smaller radius of curvature. The steps range in height from about 0.6 cm to about 4 cm in height, with a preferred height of about 1 cm. (Two steps are illustrated but more can be provided).

The cannula 2 is bent against the bolsters 33 or 36 to create the desired curvature. If a greater degree of curvature is required the cannula may be bent against the higher bolsters 34 or 35 that have a smaller radius. The symmetry of the bolsters allows the cannula to be bent to the right or to the left without having to rotate the cannula bender. This allows for a faster, easier use of the cannula bender should the need arise during surgery.

The cannula can be bent again in a different plane by rotating the cannula while maintaining the cannula bender in the same orientation. The pre-bent cannula can be contoured against the bolster in a second plane as long as the curvature is less than the height of the step of the bolster.

The entire cannula does not have to be bent, if at all. The purpose of bending the cannula is for the convenience of the surgeon in passing the suture to and from the needle(s) to the suture passer, and to manipulate the suture passer, to reach an area in the cavity or joint that would otherwise be inaccessible by a straight cannula.

Figure 8B:
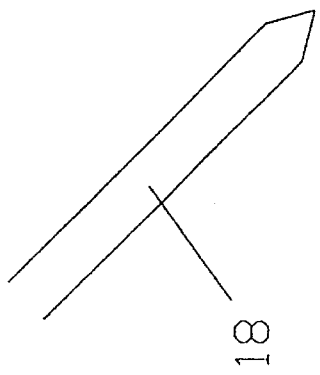
FIG. 8A is an enlarged side view of a tip of a spinal needle and FIG. 8B is an enlarged side view of a tip of an epidural needle.
Figure 8A:
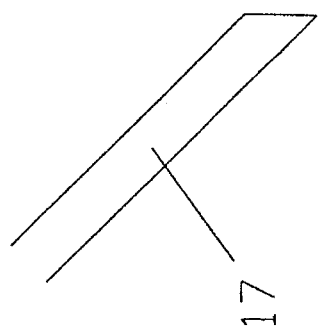

In addition to the suture passer device, the surgical repair kit also contains at least two and preferably three needles. It is preferred that the needles be epidural needles 18, two of which are of the same length, e.g., about 3.5 inches in length, and one of which is longer, e.g., about 4.75 inches in length. It is also preferred that the needles be 18 gauge needles. As seen in FIG. 8A, a spinal needle 17 has a bevelled tip which, during repair of the meniscus, may accidently lacerate the articular cartilage. In contrast, as seen in FIG. 8B, the epidural needle 18 has a Huber tip. With the epidural needle it is easier to advance the needle through tough tissue by using a twisting motion. The "rounded" tip of the epidural needle is less likely to lacerate the articular surface.

Figure 10:
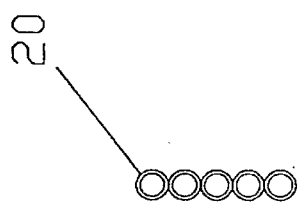
FIG. 10 is a frontal view of a parallel needle guide.
Figure 9:
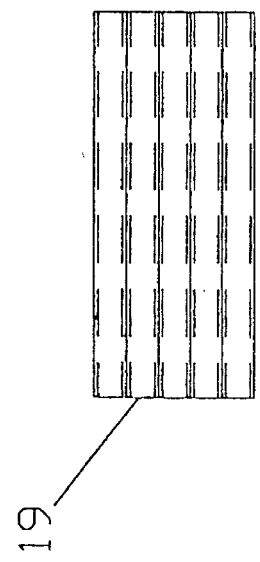
FIG. 9 is a side view of a parallel needle guide.

The surgical repair kit preferably comes with at least two needles of the same length because the needle which is inserted first becomes blunt after several insertions. The insertion of the second, generally longer, epidural needle is easier with the use of the parallel needle guide 19 as shown in FIGS. 9 and 10. (Longer and shorter needles are utilized to prevent the hubs 29A of adjacent needles from interferring with one another by staggering the hub distance from the patient's body). The parallel needle guide allows for the proper alignment of the needles through which the suture will pass. The parallel needle guide is a series of at least three, and preferably four to five hollow tube shaped units 20 longitudinally adhered to each other one on top of the other in a parallel formation. The opening or diameter of each tube shaped unit should be large enough to allow for the passage of an 18 or 21 gauge needle to pass through. The parallel needle guide may be made out of plastic, paper or metal. The parallel needle guide may be from a mold, or the individual tubes may be individually formed and bonded to each other. Any method of forming the structure is acceptable.

Figure 11:
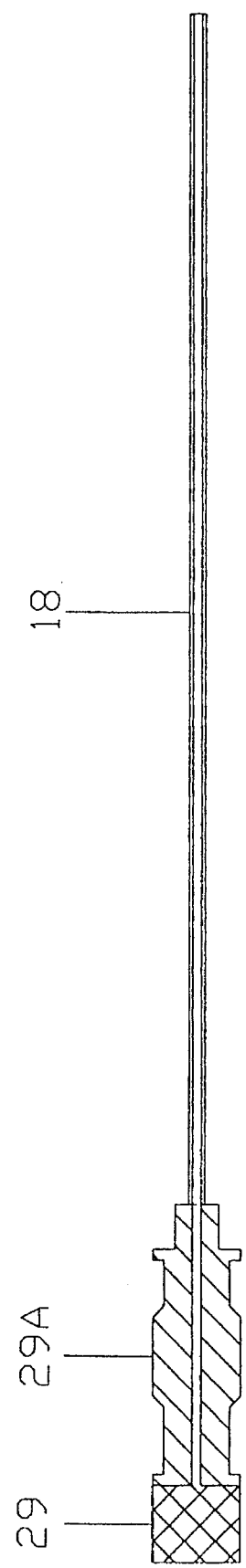
FIG. 11 is a side section view of a needle containing a stylet.

Additionally, there is at least one stylet typified by stylet 29 shown in FIG. 11 in the surgical repair kit for each needle included in the repair kit. The stylet is kept in the needle until the needle is passed through the meniscus. This prevents the needle(s) from being clogged with tissue and cartilage as it is pushed through the cartilage. A needle clogged with tissue will, of course, not allow the suture to be passed through the needle to the suture passer.

A template (not shown) is preferably included in the surgical repair kit. This template, which may be printed on the back of the surgical repair kit container, may be printed on a paper guide inside the meniscal repair kit, or may be provided on, or as, a plastic guide. The template is used as a guide for the bending of the cannula.

Each of the items included in the surgical repair kit is sterile. Additionally, each item in the surgical repair kit is preferably individually packaged in sterile plastic, paper, metal foil, or combinations thereof. The packaging should be easy to open, so that the contents thereof are not damaged or do not fall on the operating floor while opening. The content of the package and the packaging may be sterilized with ethylene oxide or by radiation, or any other conventional method for the sterilization of packaged elements.

The surgical repair kit which includes the suture passer, at least two surgical needles of predetermined length, and at least one stylet for each needle, may also contain an optional third needle of greater length than the other two needles, the parallel needle guide, and a template. If the cannula is made of metal, a cannula bender may be included in the repair kit. While the repair kit may be used for any surgery, the repair kit is extremely useful in meniscal repair.

Figure 14:
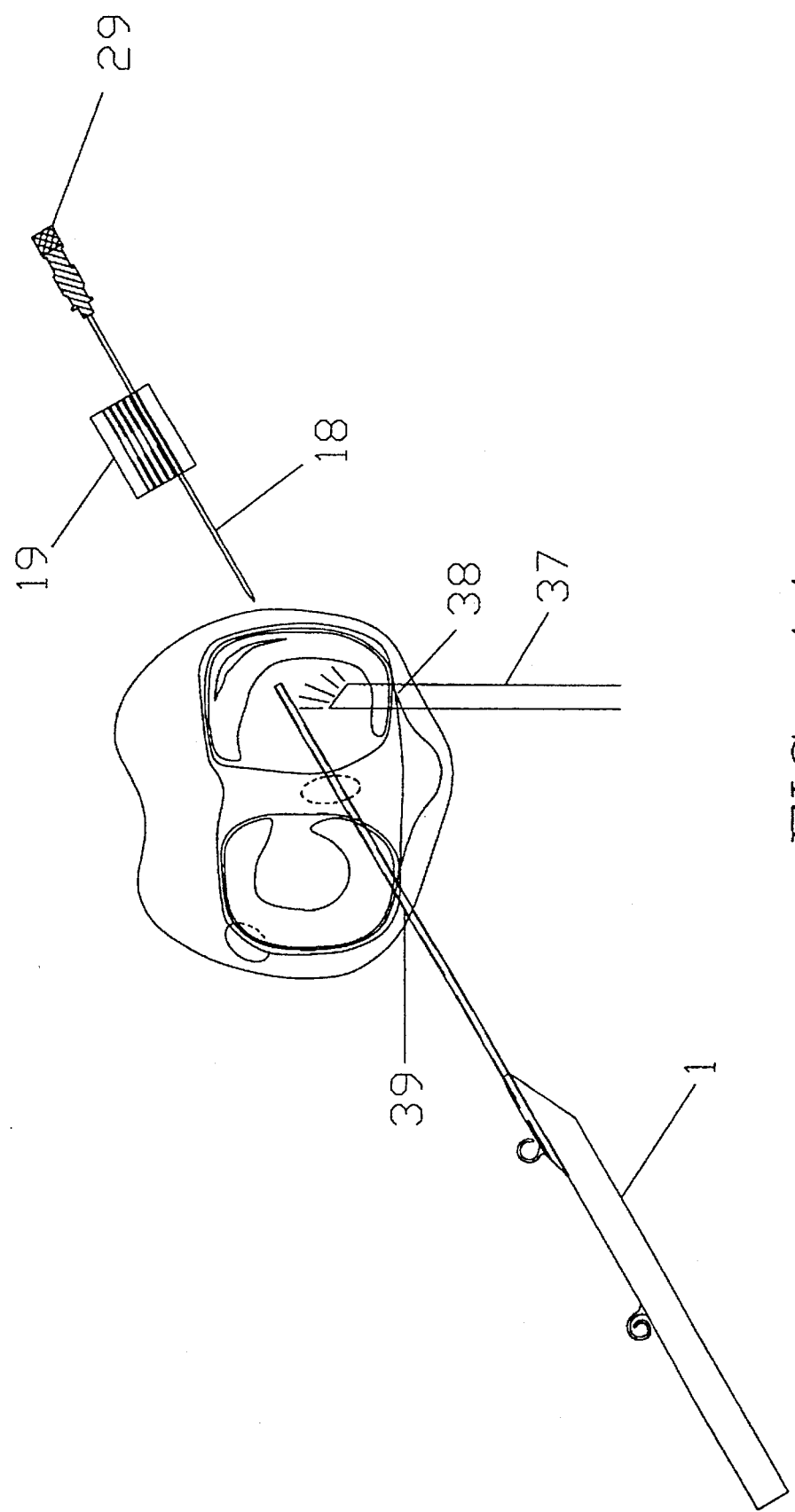
FIGS. 14, 15, 16, 17, 18, 19, 20, 21, 22, 23, 24, 25 and 26 are cross-sectional top views at various stages of an operation where the middle third of the meniscus is being repaired.

In repairing the middle third of a meniscus, an arthroscope 37 should enter through an ipsilateral portal 38 as shown in FIG. 14. The suture passer 1 should enter through the contralateral portal 39. The epidural needle is loaded through the hole on one end of the needle guide using a one handed technique to avoid accidental puncture of the surgeon's opposite hand.

There are three methods of identifying the insertion points for the needles.

The first method is to view the meniscal tear with the arthroscope, with the synovial meniscal junction in view, and then advance the arthroscope to the synovial meniscal junction. The light from the arthroscope will transilluminate the skin. The point of insertion of the epidural needle should be slightly distal to this light.

The second method of determining where to insert the needles is to view the meniscal tear and to keep the synovial meniscal junction in view. Palpate along the joint line with a tip of a finger or a meniscal probe. The area of maximal wall motion at the synovial meniscal junction indicates the point at which the epidural needle should be inserted.

The third method is the easiest method in determining the needle insertion point, if the synovial meniscal junction is accessible to the suture passer. The tip of the suture passer is pushed against the synovial meniscal junction and the skin is palpated, with the finger. The area of the tip will indicate the approximate location where the needle should be inserted.

Figure 15:
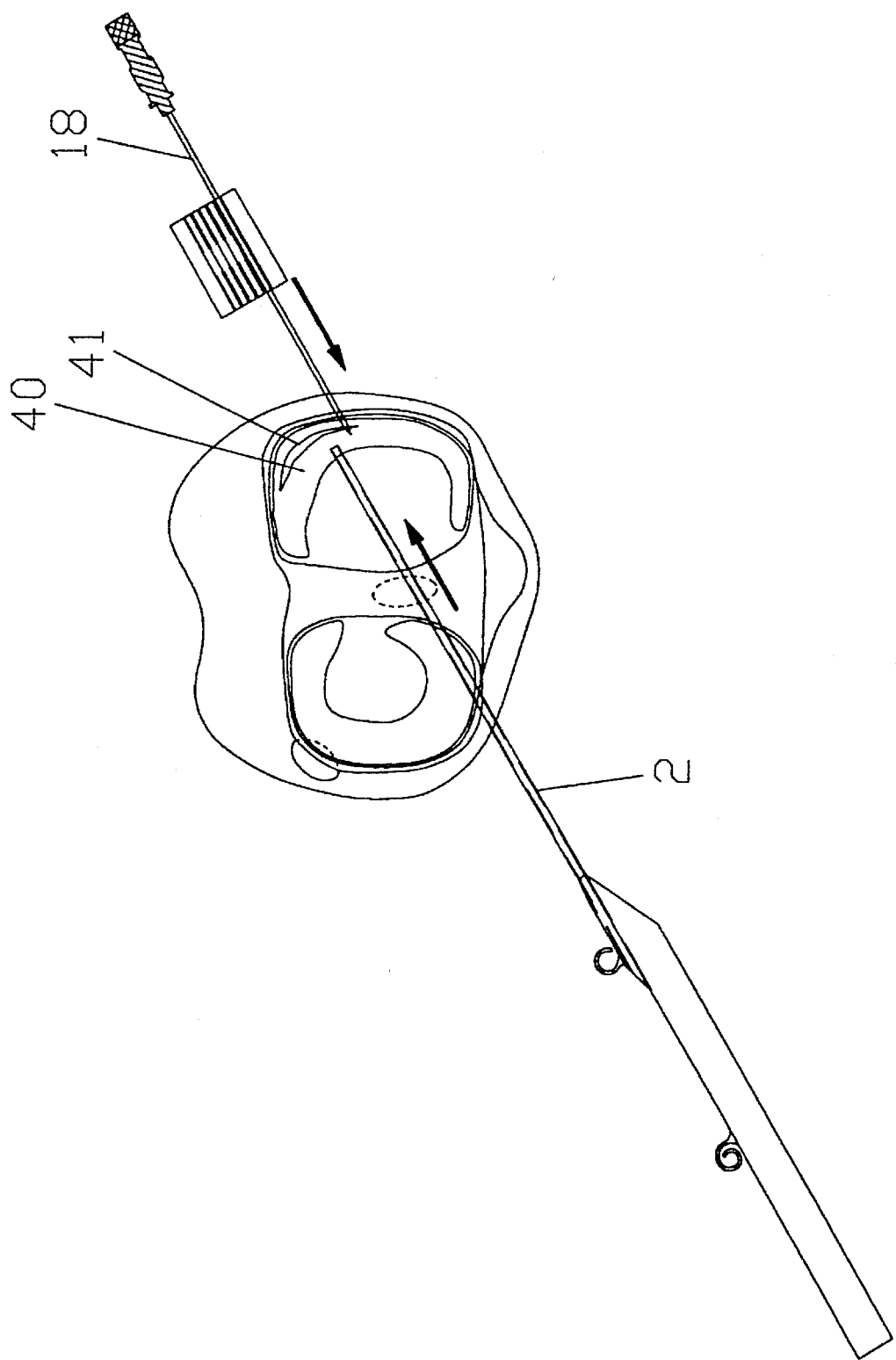

The needles may be advanced with a twisting motion if difficulty is encountered in penetrating the tough meniscal tissue. As shown in FIG. 15, an inner rim 40 of a meniscal tear 41 may be buttressed with the tip of the cannula 2 of the suture passer to stabilize it against the advancing needle 18.

Figure 16:
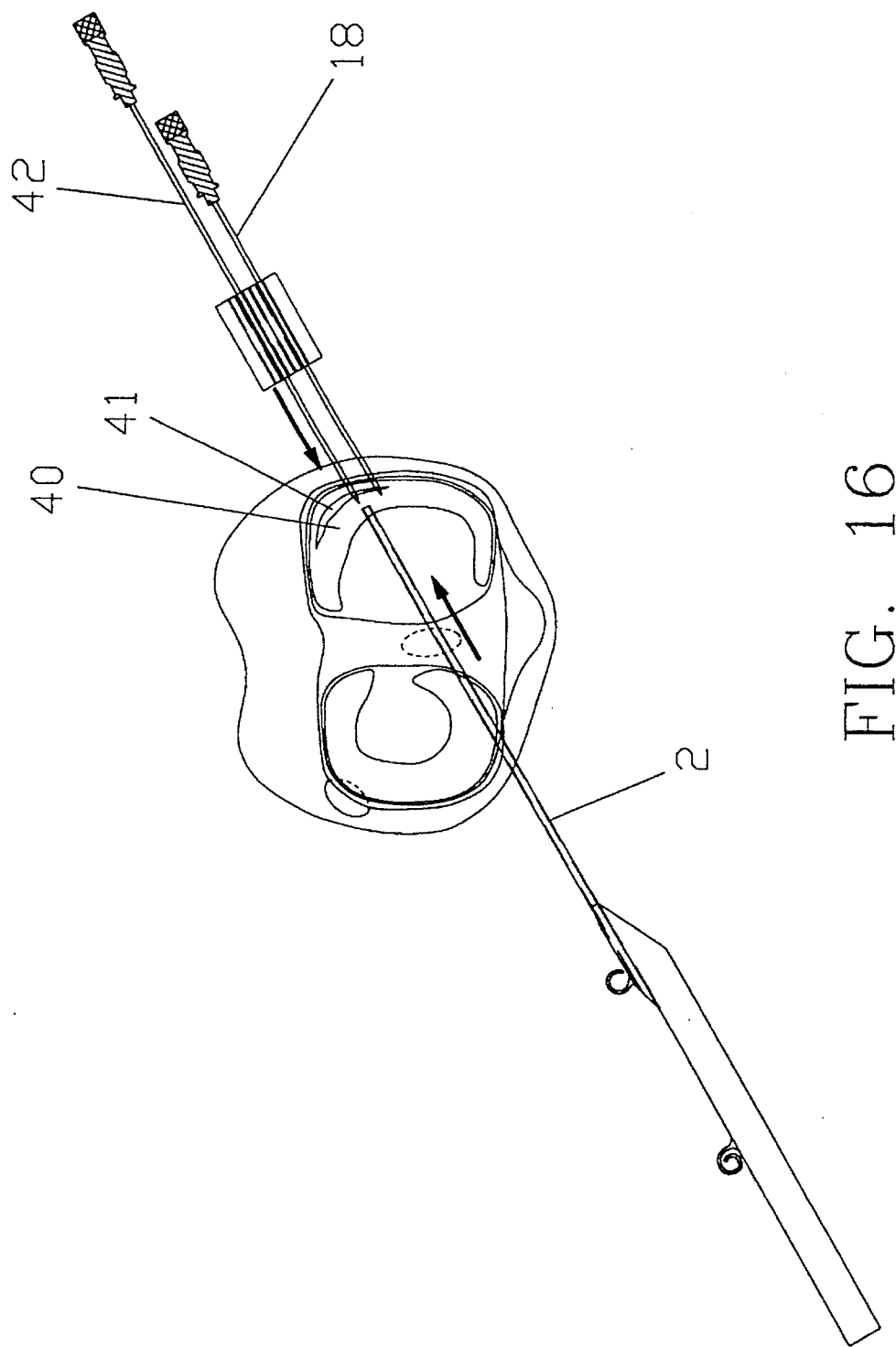

Using the parallel needle guide, two epidural needles are inserted through the guide and across the meniscal tear with a long epidural needle 42 being inserted through the needle guide at a desired separation distance from the shorter needle (as shown in FIG. 16). This longer needle is inserted through the meniscal tissue, preferably behind the shorter needle. The stylets are removed from the needles. A suture is passed through the "first" needle. The tip of the cannula of the suture passer is introduced into the joint cavity through a small incision. The distal opening of the cannula is placed at or near the opening of the needle through which the suture has been passed. There are areas in the joint cavity, although visible through the arthroscope which are not accessible with a straight cannula. Consequently, prior to the introduction of the suture passer, the cannula of the suture passer may be bent on the cannula bender. The curved cannula allows the surgeon to reach remote areas where the meniscus is being repaired.

Figure 17:
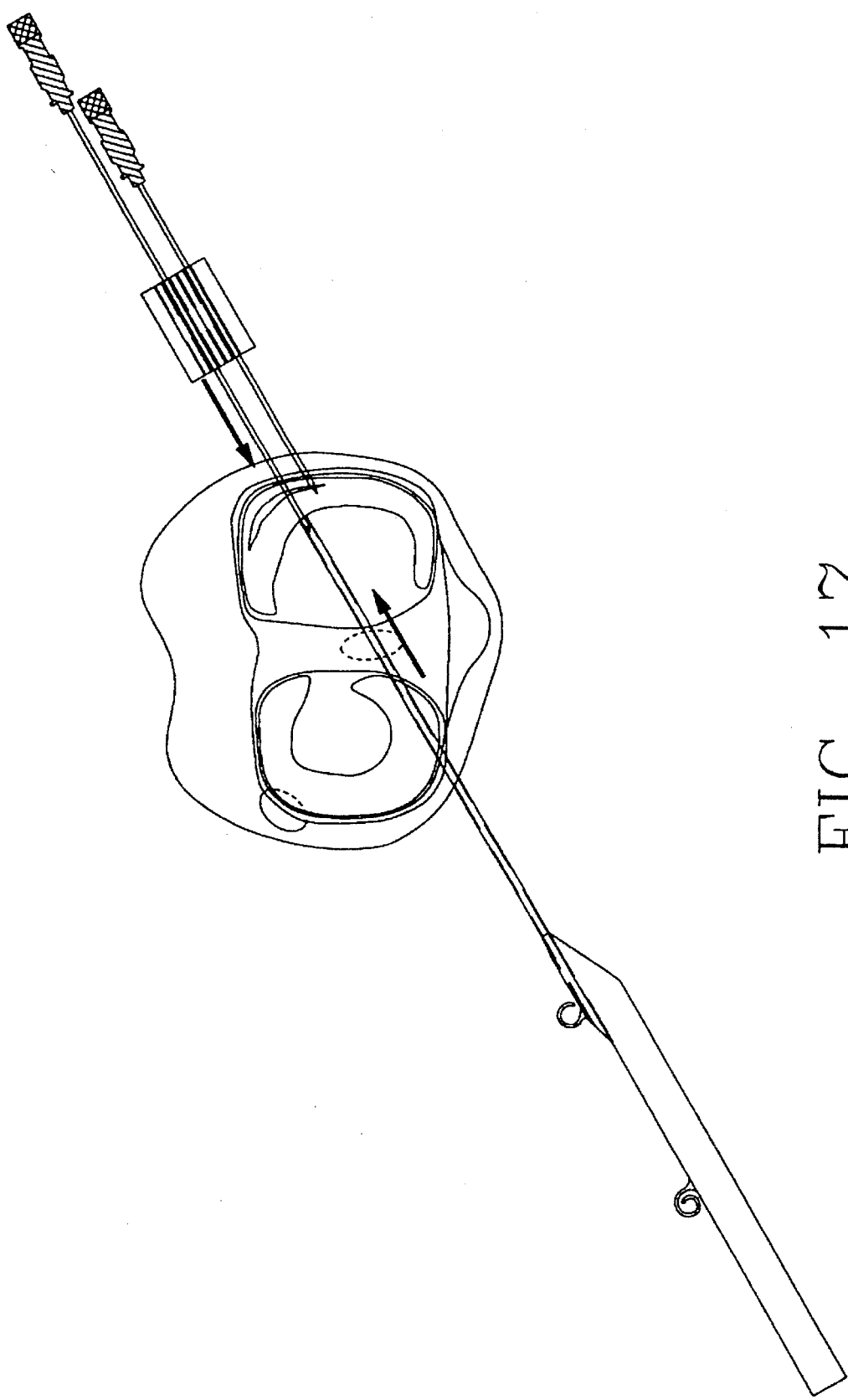

In a preferred method for passing the suture from the cannula to the needle, the needle, preferably an epidural needle with a Huber tip, engages the opening of the cannula (FIG. 17). The more posterior needle is advanced into the joint and captures the tip of the needle with the tip of the cannula. For ease of passage, it is preferable that the cannula and needle meet at about a 15°–30° angle. The opening of the needle should be facing away from the apex of engagment between the cannula and the needle. The suture is passed directly from the cannula into the tip of the needle or vice versa.

Figure 18:
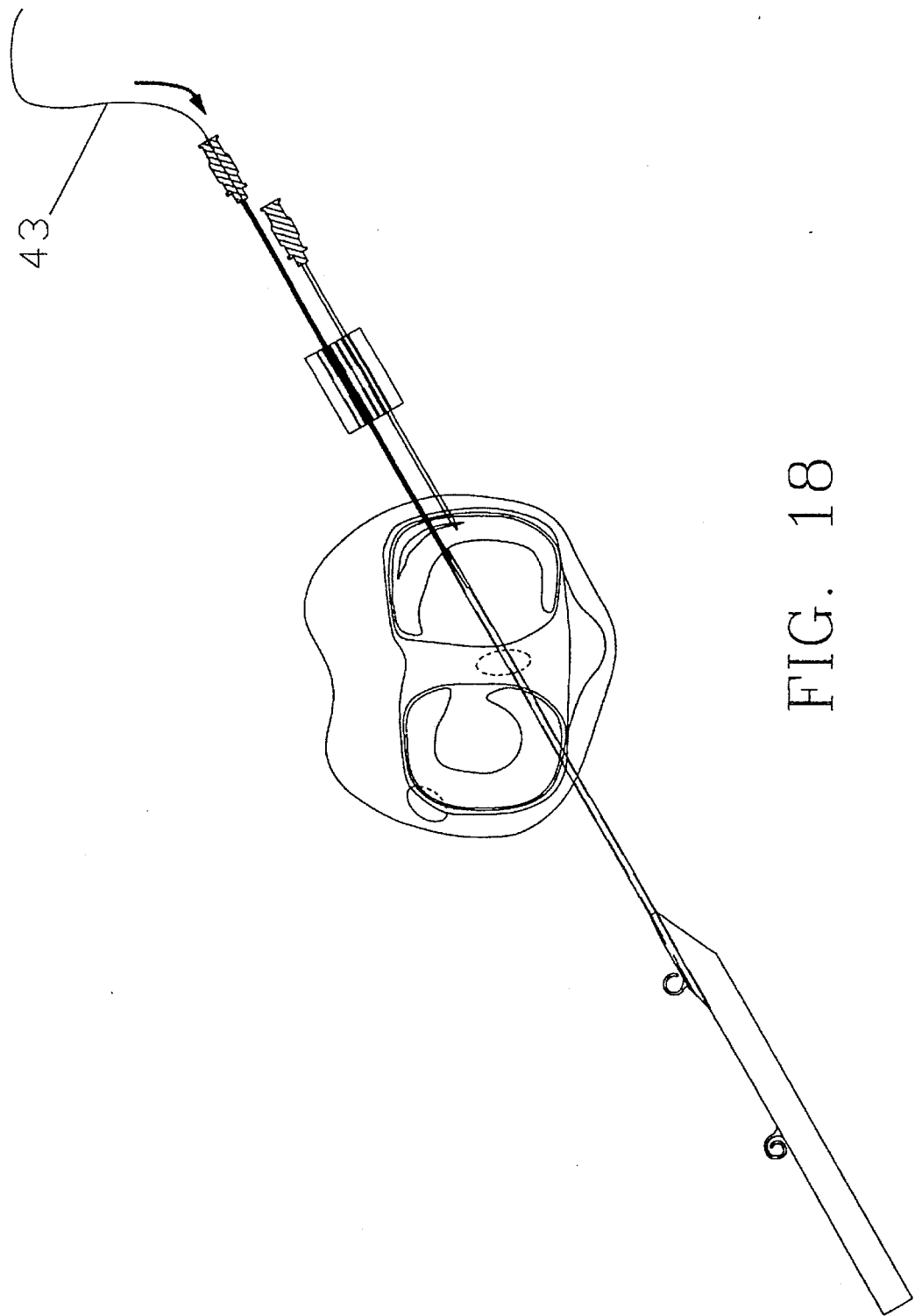
Figure 19:
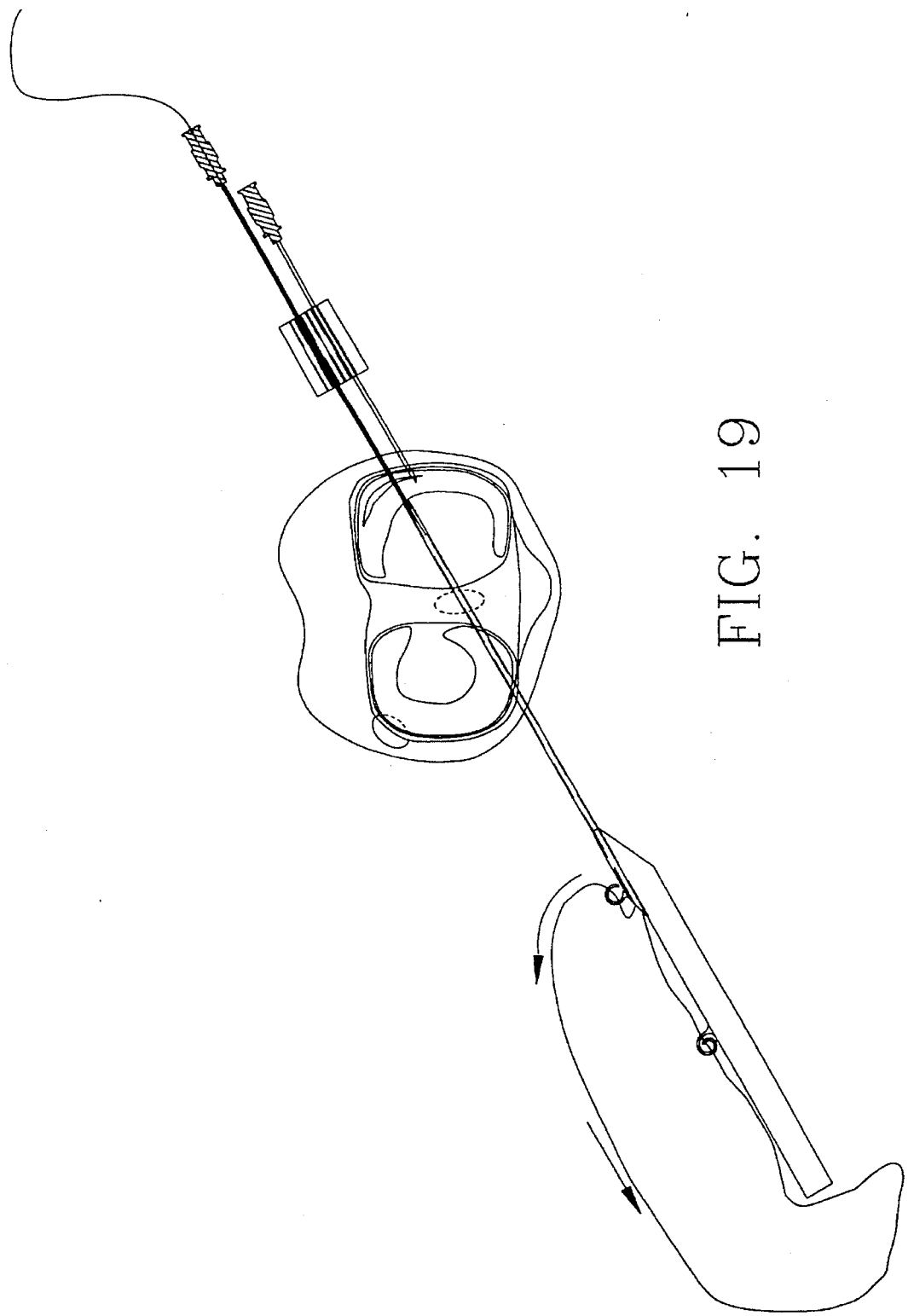

By careful manipulation, a suture 43 is fed through the needle and into the cannula. With the tip of the cannula and the needle securely engaged, the suture is fed (FIG. 18) into the hub of the needle until it exits the proximal opening of the handle of the suture passer. It is advisable to pull the suture three quarters of the way through. The suture close to the opening 4 of the cannula is brought forward to engage the proximal loop. The suture is looped onto the distal guide and is threaded back into the cannula. The suture is engaged onto the proximal guide (FIG. 19).

Figure 20:
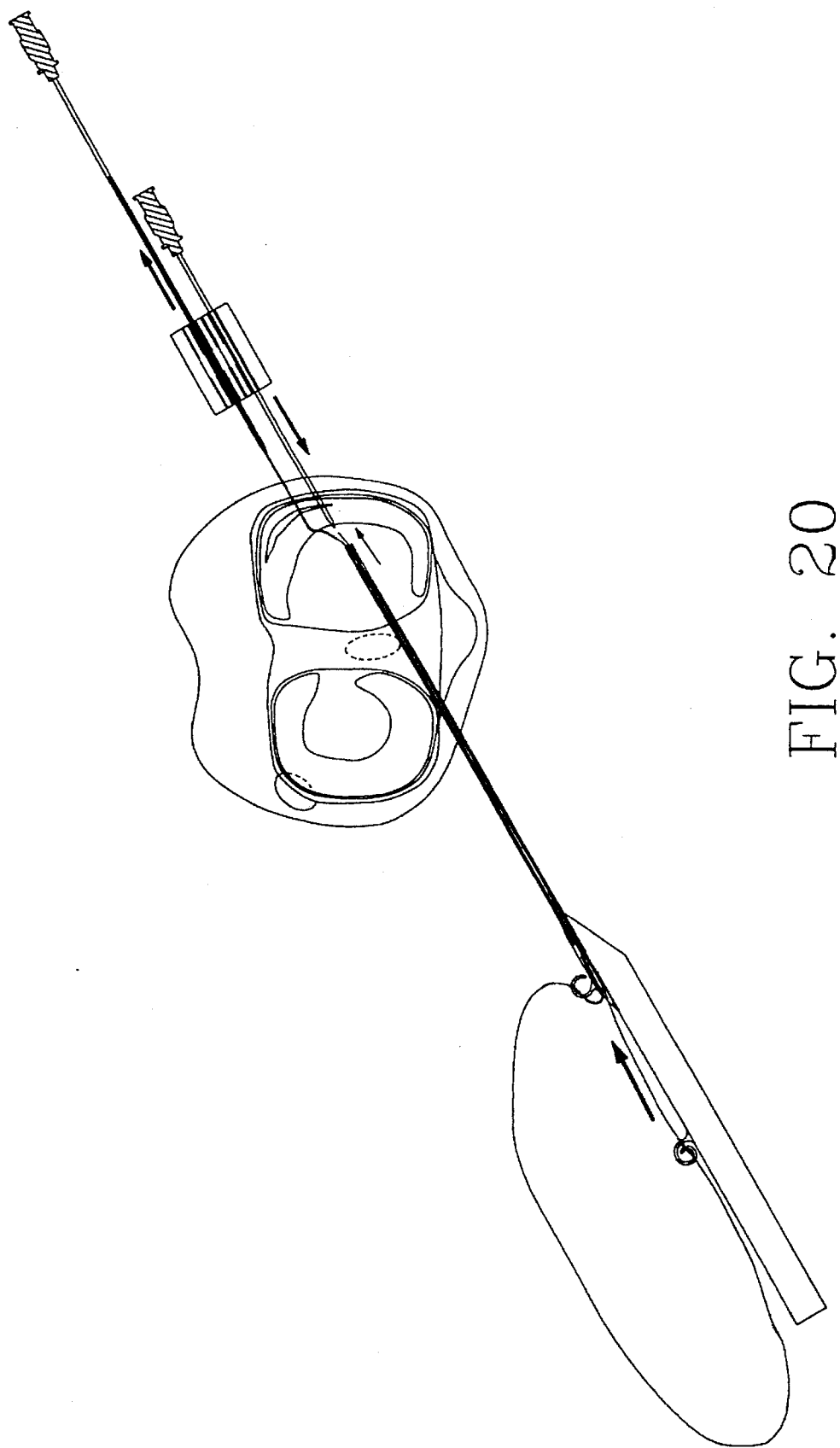
Figure 21:
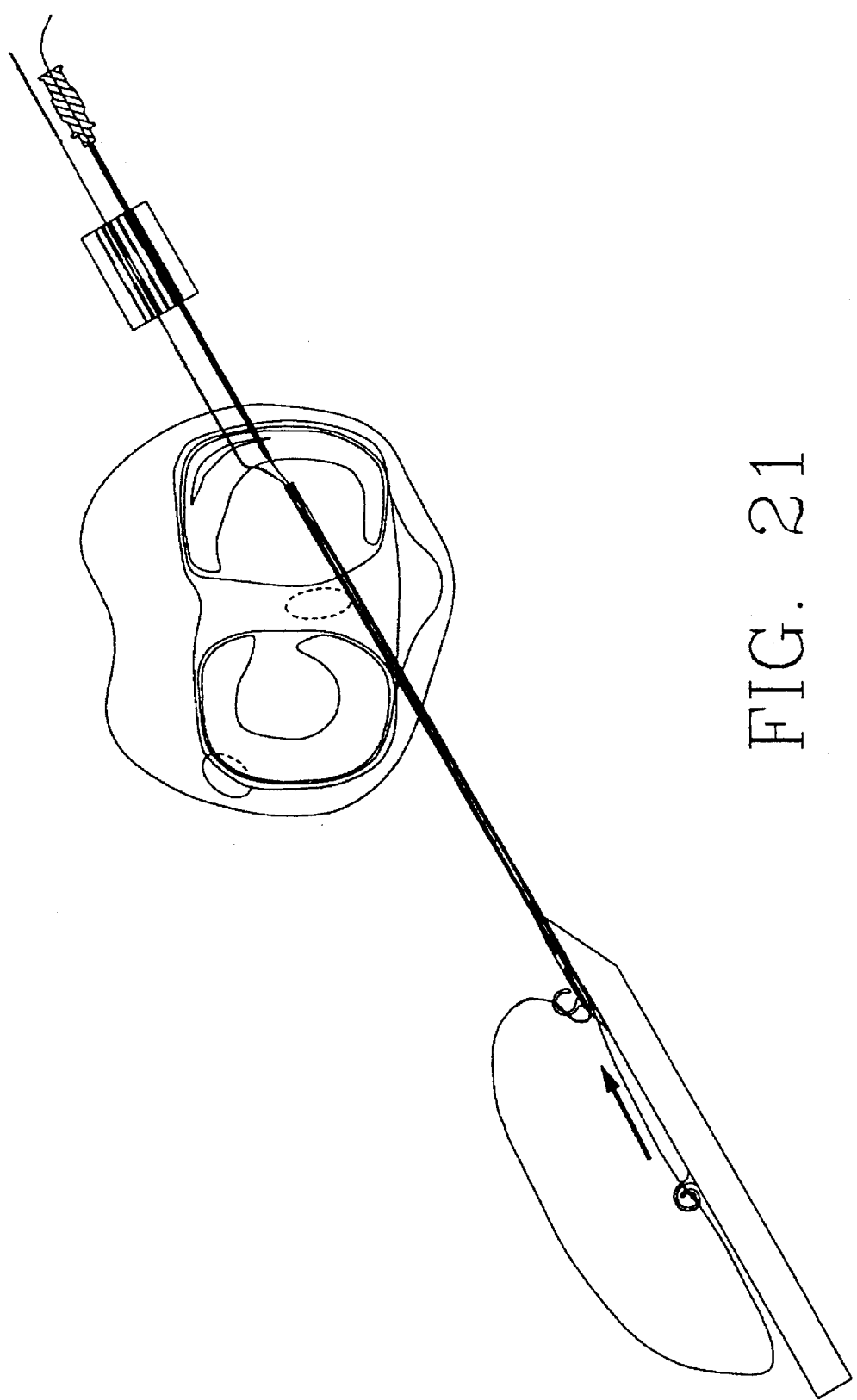
Figure 22:
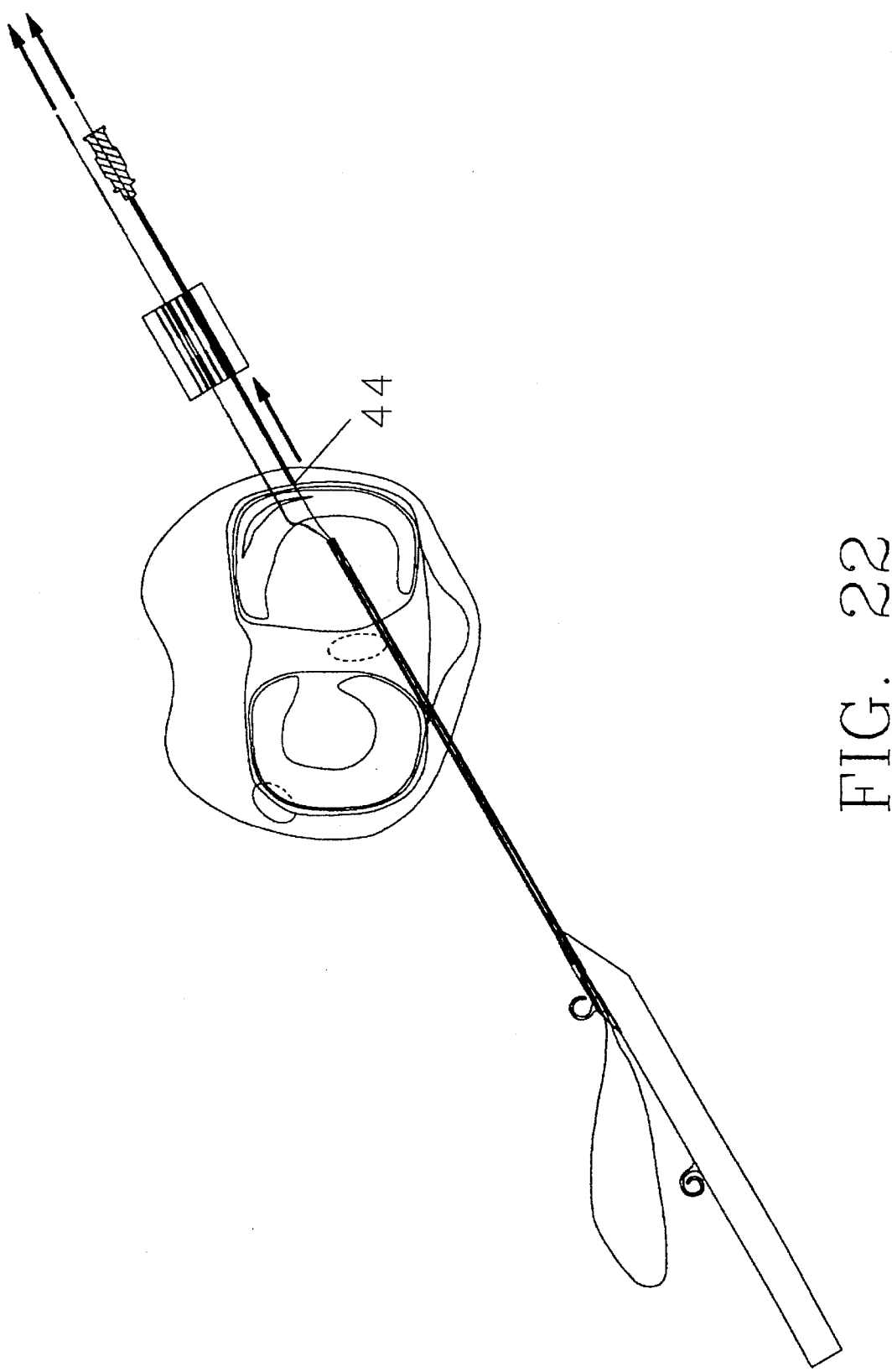

The first needle is removed, and with the two limbs of the suture held separately by the proximal and distal loops, one limb of the suture is advanced by sliding the suture with the index finger over the top surface of the handle so that the suture emerges from the tip of the cannula (FIG. 20). The suture, via the suture passer, is now fully controllable with one hand. The tip of the second needle and the tip of the cannula are brought into close proximity and the suture is passed from the loaded suture passer into the opening of the second needle and through the second needle. The suture is advanced until it exits from the hub of the second needle (FIG. 21). The second needle is partially removed so that the tip of the second needle is buried within soft tissue 44 (FIG. 22). The suture is disengaged from the guides on the handle of the suture passer.

Figure 23:
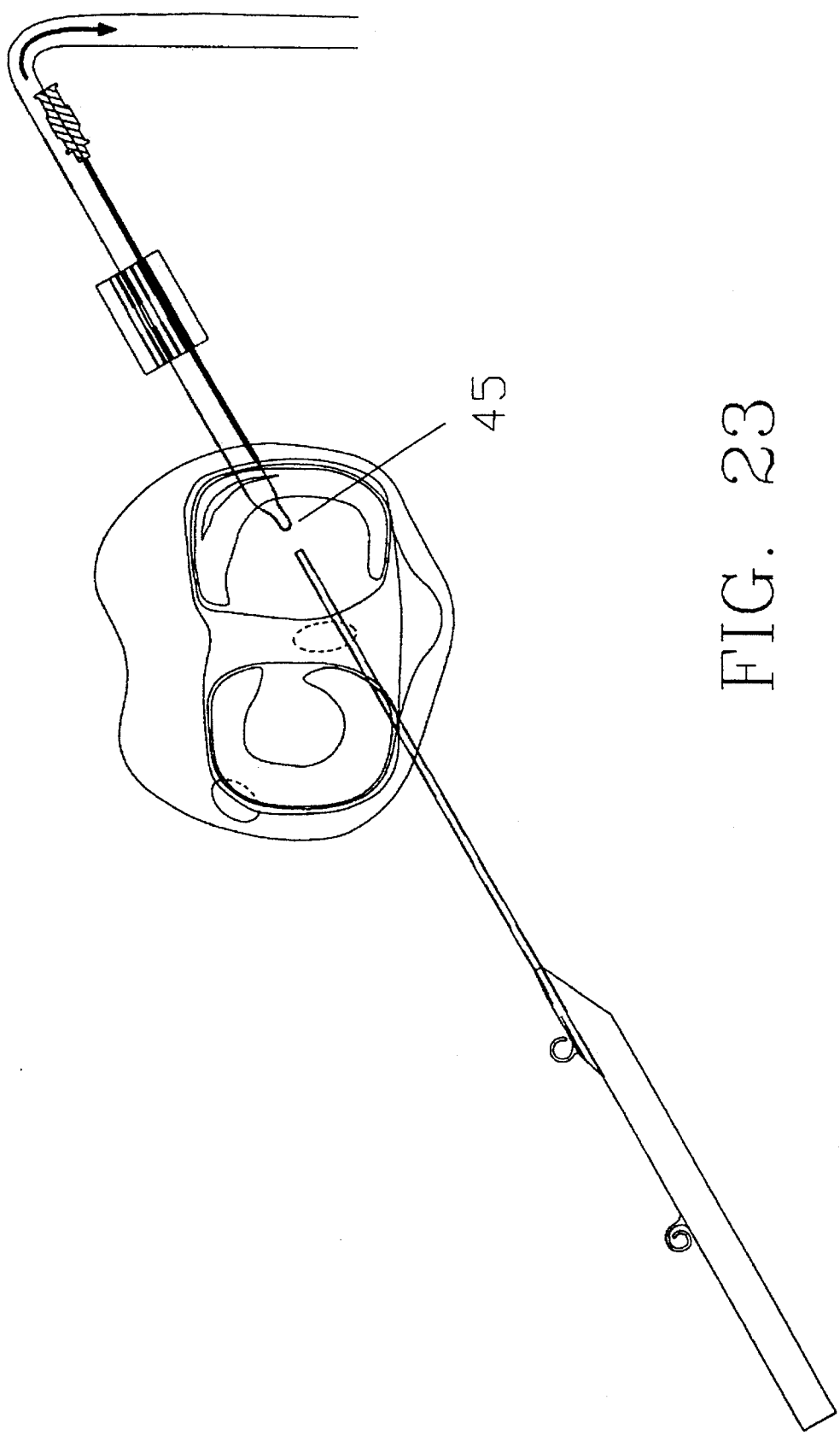
Figure 24:
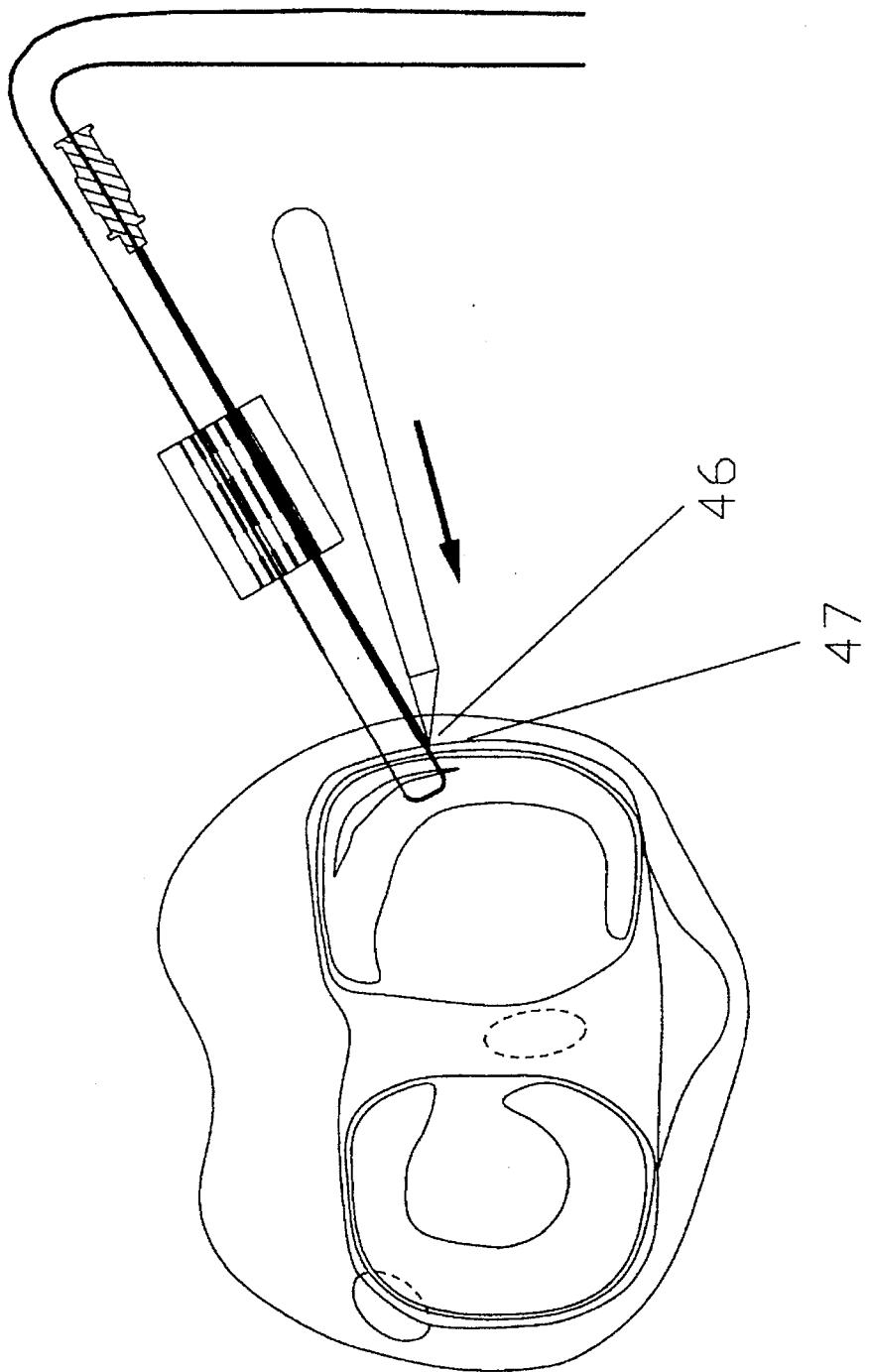
Figure 25:
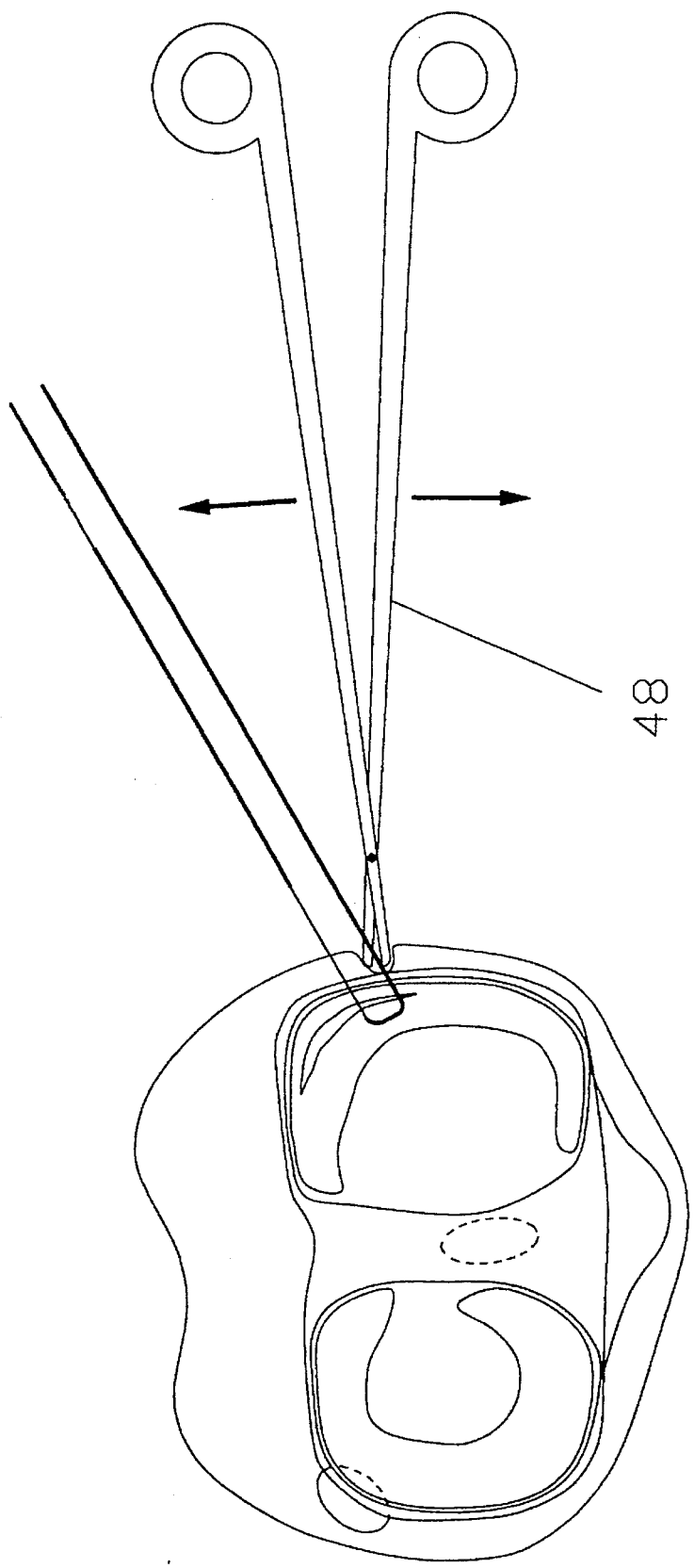
Figure 26:
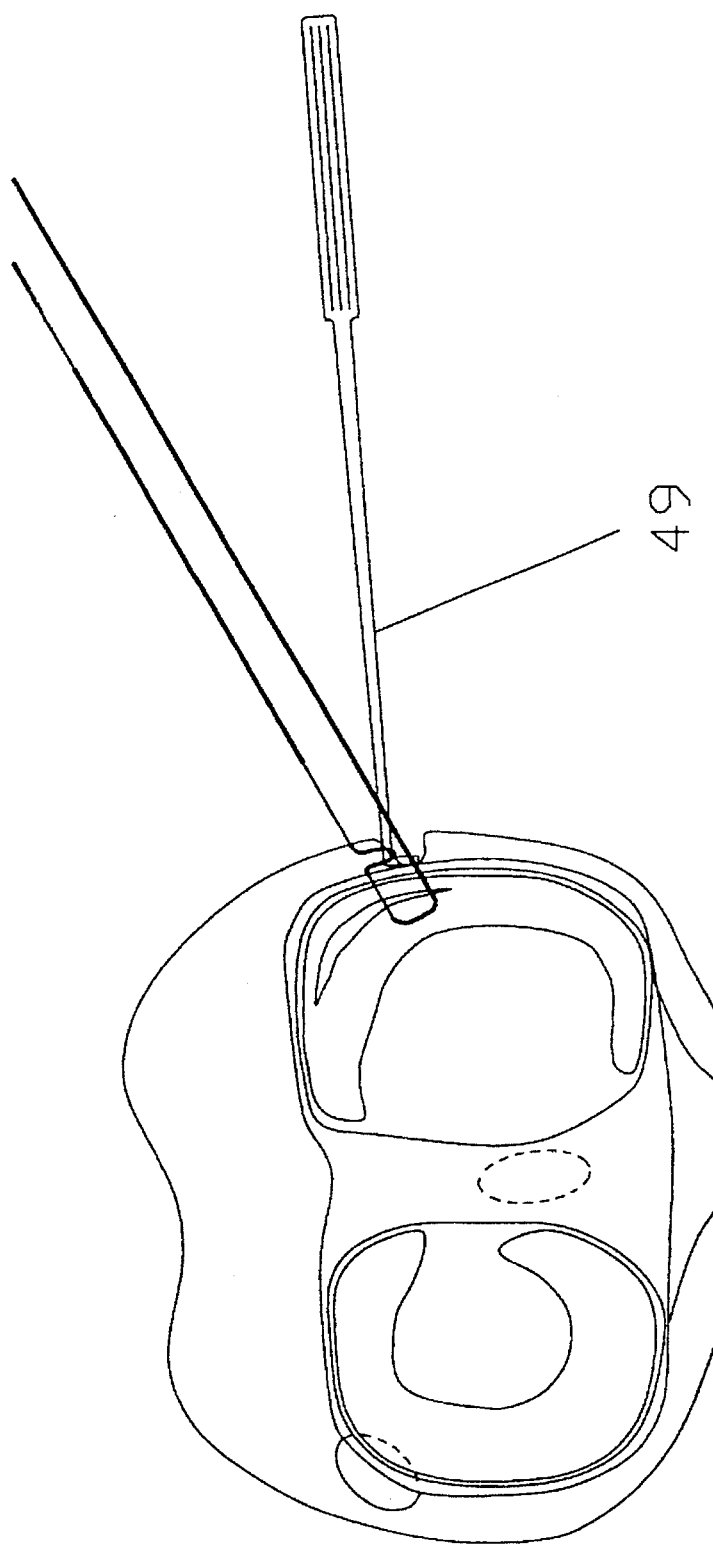

While grabbing both ends of the suture, the suture is pulled through the cannula into joint 45 (FIG. 23). With the second needle still in place, a stab incision 46 is made along the shaft of the second needle down to the level of a joint capsule 47 but not beyond (FIG. 24). The second needle is removed and the soft tissue is dissected all the way down to the joint capsule by spreading the soft tissue with a pair of small forceps 48 (FIG. 25). The other limb of the suture is then retrieved through this "stab incision" with a meniscal probe 49 (FIG. 26) and the sutures are tied after all of the sutures have been put into place.

Figure 27A:
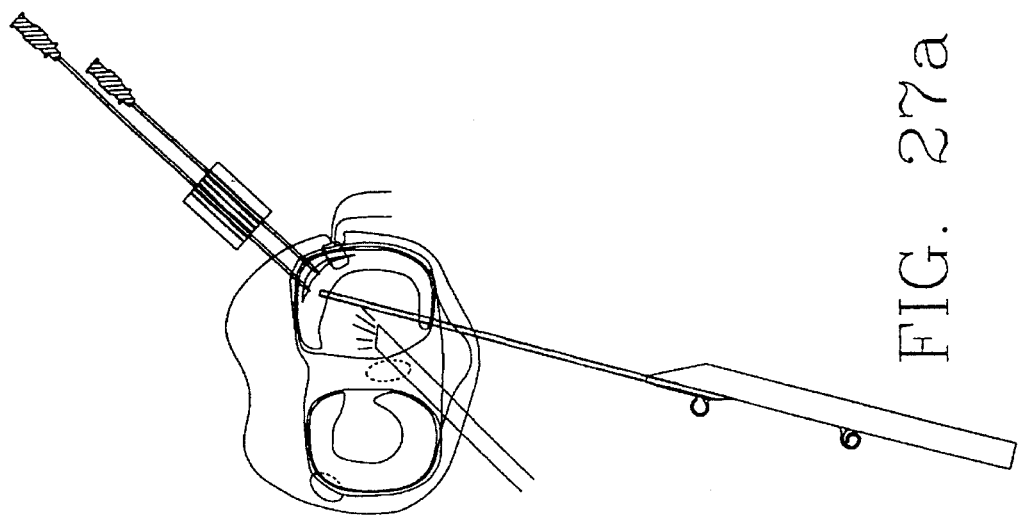
FIGS. 27a, 27b, 28, 29, 30 and 31. are cross-sectional top views at various stages of an operation where the posterior region of the meniscus is being repaired.
Figure 27B:
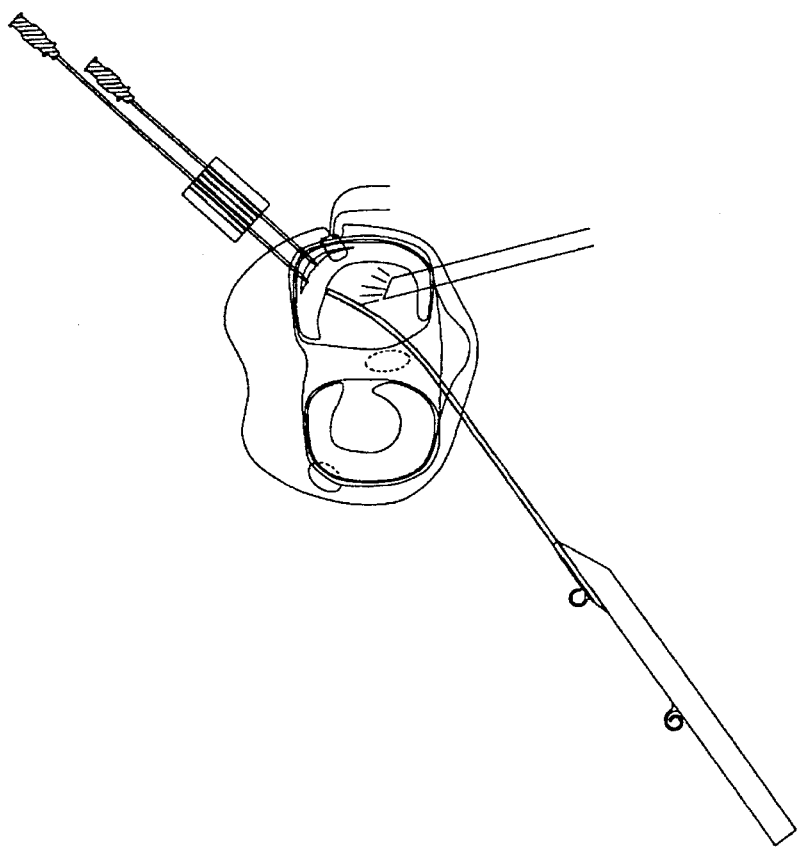

For a meniscal tear in the more posterior position, the straight cannula can enter through the ipsilateral portal to reach the posterior horn of the meniscus (FIG. 27a). The cannula can also be contoured to reach a specific zone of the meniscus with the use of the cannula bender and the template for the various zones (FIG. 27b).

Figure 28:
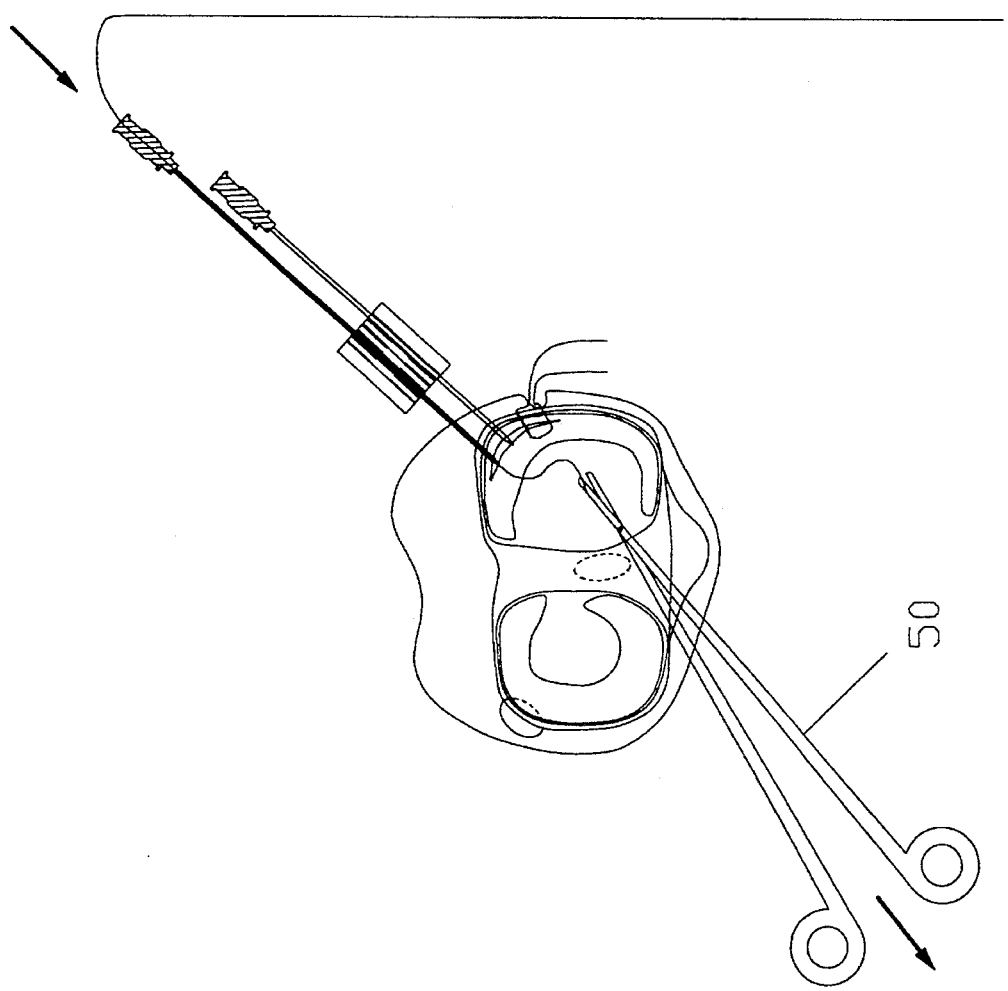
Figure 29:
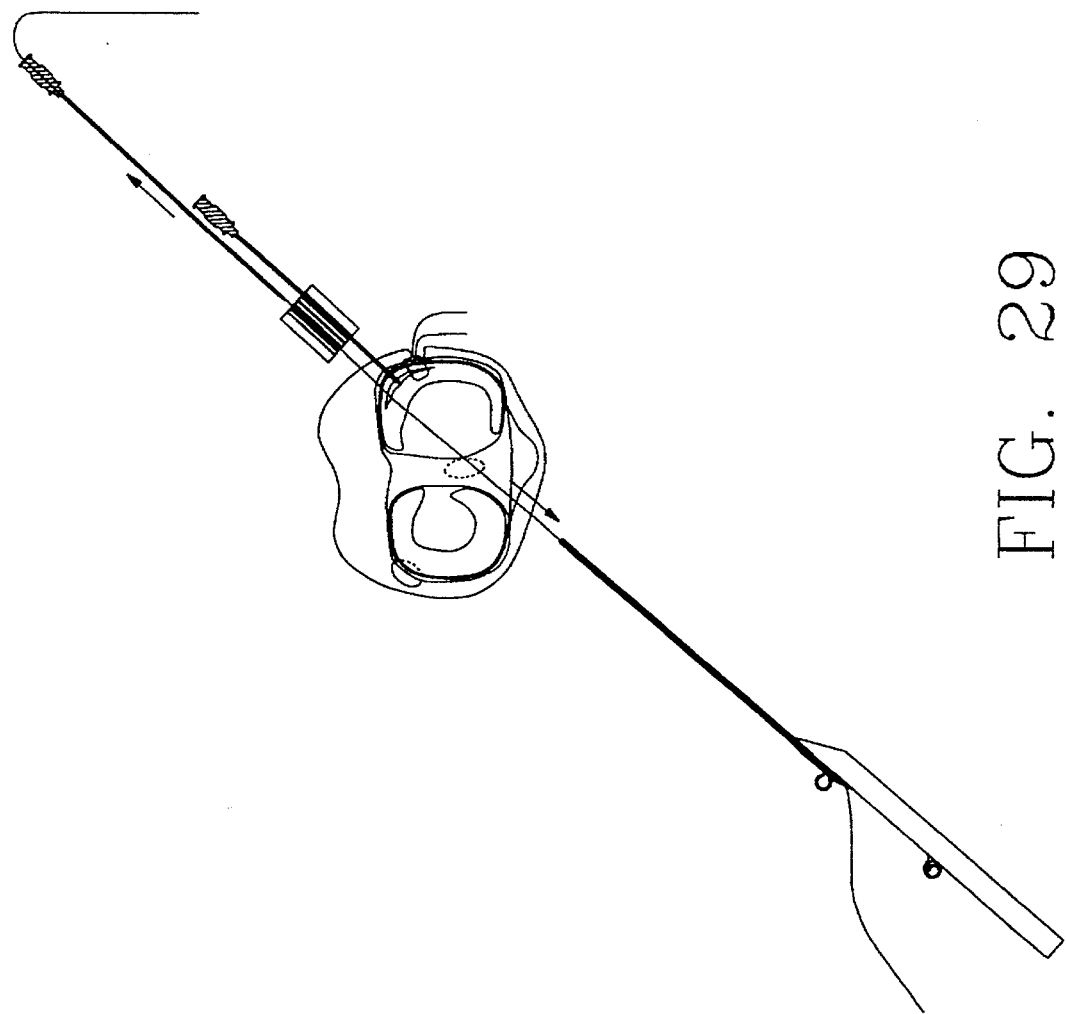
Figure 30:
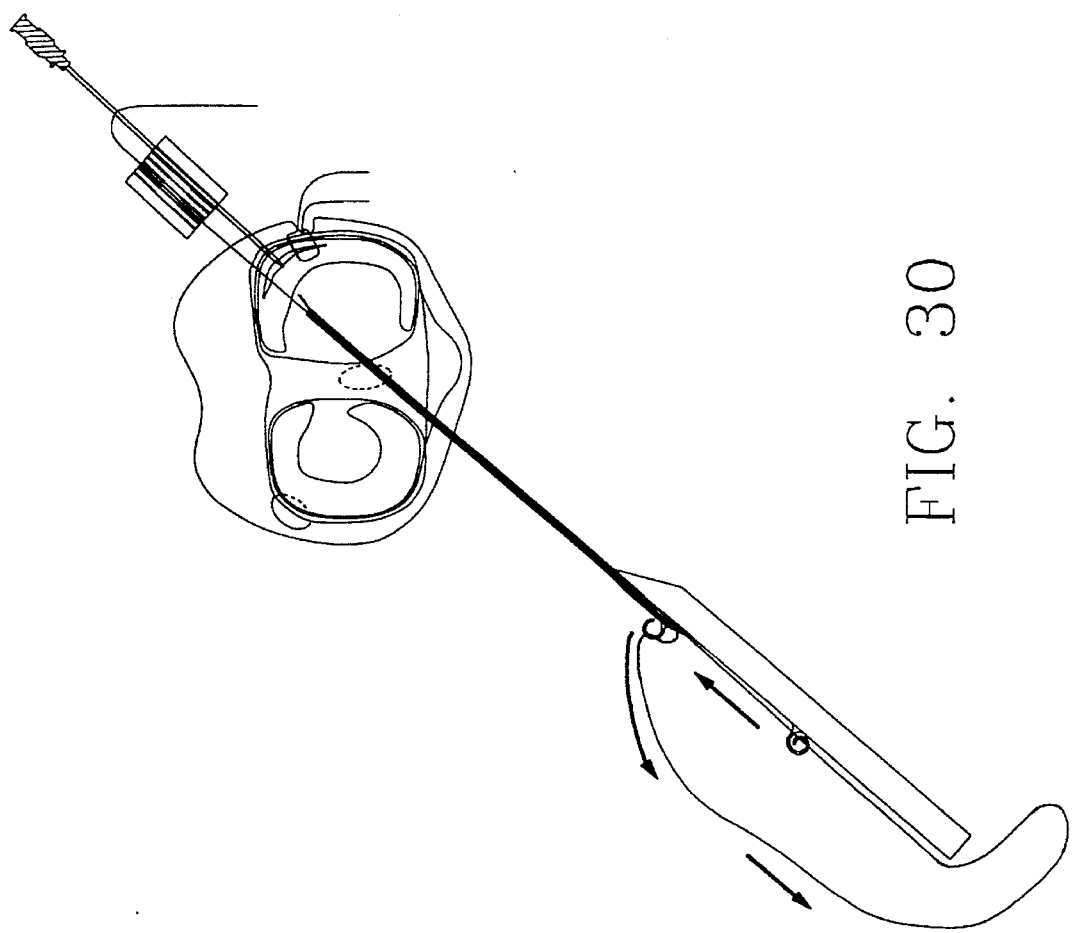

During repair of the meniscus, if the tip of the cannula cannot engage the tip of the needle during initial passage of the suture, the suture may be fed through the posterior needle into the joint. The suture may then be retrieved with a snap or a suture retriever 50 (FIG. 28). The first needle is removed and the suture is fed into the cannula in a retrograde direction (FIG. 29). The cannula is advanced into the joint along the suture. The suture is then looped onto the distal guide and threaded back into the cannula until it reaches the tip of the cannula. The suture is then engaged onto the proximal guide (FIG. 30).

Figure 31:
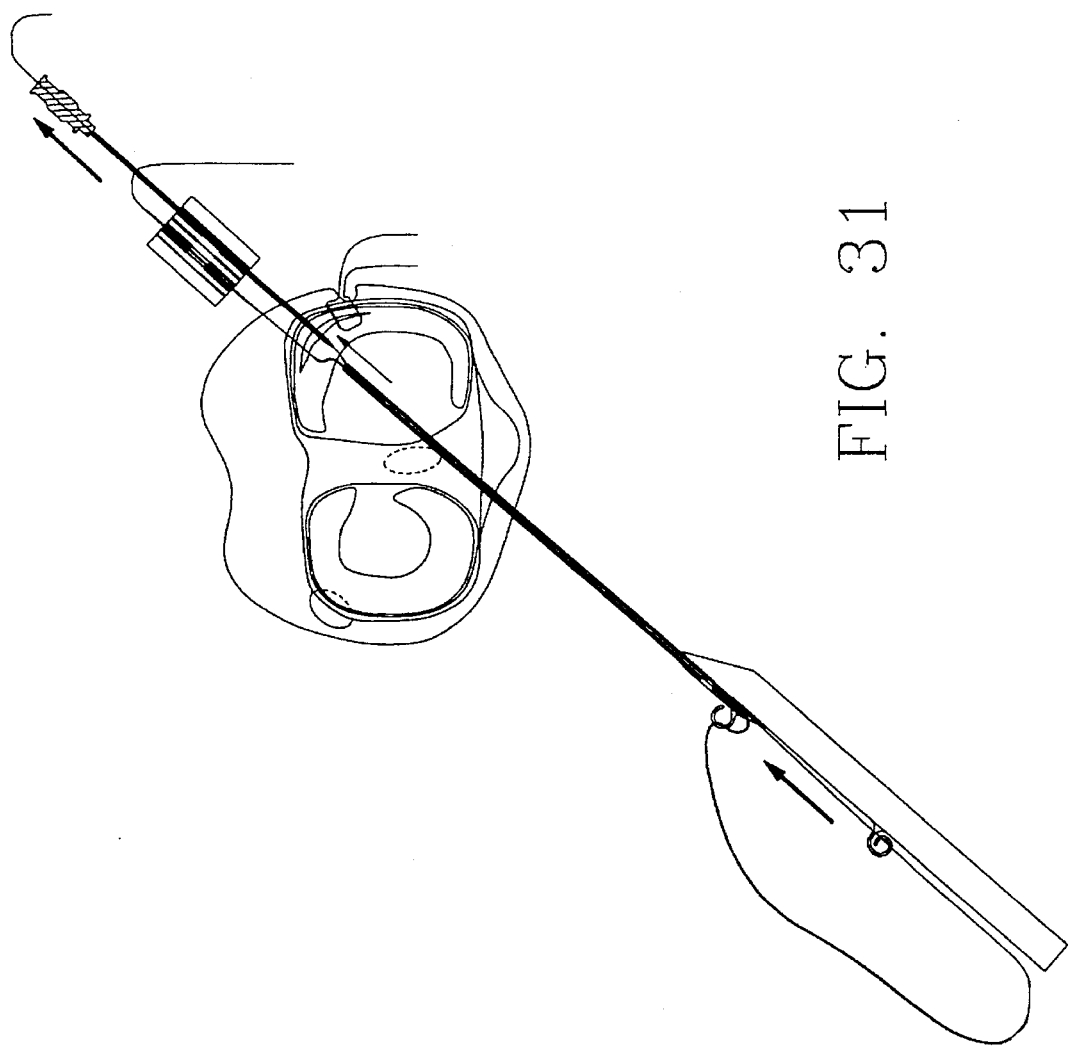

The suture is then advanced into the tip of the second needle under arthroscopic visualization (FIG. 31). The suture is advanced until it exits from the hub of the second needle. The second needle is slightly pulled back so that the tip of the needle is buried within the soft tissue. The suture is disengaged from the guides on the handle of the suture passer and the suture is pulled through the cannula into the joint.

The suture passer can also be used to pass the suture from the suture passer to the hollow needles, instead of vice versa. The suture passer is loaded with a suture so that the suture engages the first and second guide means with the "beginning" and "terminal" ends of the suture protruding from the distal opening of the hollow cannula. The beginning end of the suture is fed from the distal opening of the hollow cannula through the opening of the first hollow needle until it exits the first hollow needle. The terminal end of the suture is passed from the distal opening of the hollow cannula through the opening of the second hollow needle until it exits the second hollow needle. The suture is then completely disengaged from the suture passer, the suture passer is removed, both hollow needles are removed and the suture is tightened and tied.

By maneuvering the tip of the needle with one hand and the cannula in the other when both tips are in close proximity, the suture may be advanced.

In another method, the suture protrudes from the cannula by about ½ to 1 centimeter. By manipulating the tip of the cannula with the tip of the needle, one can engage the suture into the tip of the needle and advance the suture.

An arthroscopic video camera may be used to visualize the suturing. The surgeon manipulates the suture preferably while viewing a video monitor connected to the camera.

A recommended suture for use is the Ethicon "0" PDS suture. The length of the suture should be at least 27 inches and preferably 36 inches in length. With other types of monofilament suture, the strand tends to be curled when removed from the packaging. It is necessary to straighten out the suture prior to use, as the ends of the suture must be straight for ease of passage of the suture between the cannula and the needle.

It is preferable that the suture being used have distinct markings to give an enhanced visual indication of the movement of the suture. Different types and colors of markings along the length of the suture will indicate how much suture has been advanced. It is preferred that the suture have distinct markings at the beginning and terminal ends of the suture, which could indicate the length of the suture which has been advanced.

If the meniscal tear is large, the repair operation should begin at the anterior portion of the tear. After the placement of the anterior suture, it will be easier to work along the anterior joint line to the posterior part of the tear. The medial meniscus is repaired with the knee in near extension or slight flexion. The lateral meniscus is repaired with the knee in 45° to 90° flexion.

The foregoing description of the preferred embodiments of the invention has been presented for the purposes of illustration and description. It is not intended to be exhaustive or to limit the invention to the precise forms disclosed. Many modifications and variations are possible in light of the above teachings. It is intended that the scope of the invention not be limited by this detailed description.

What is claimed is:

1. A suture passer comprising:

a longitudinally extending hollow cannula having a central passage slidingly receivable of a surgical suture;

a manually graspable handle connected to said hollow cannula for manipulation thereof, said handle having an upper outer surface, said hollow cannula being connected to said upper outer surface of said handle;

first guide means, connected to said upper outer surface of said handle at a location approximate a proximal end of said handle, for releasably, guidingly, holding the surgical suture;

second guide means, connected to said upper outer surface of said handle at a location longitudinally displaced from and distal to said first guide means, for releasably, guidingly, holding the surgical suture; and wherein said hollow cannula terminates at a rearward opening located intermediate the locations of said first and second guide means.

2. A suture passer comprising:

a longitudinally extending hollow cannula having a central passage slidingly receivable of a surgical suture;

a manually graspable handle connected to said hollow cannula for manipulation thereof, said handle having an upper outer surface said hollow cannula being received within a bore formed in said handle;

first guide means, connected to said upper outer surface of said handle at a location proximate a proximal end of said handle, for releasably, guidingly, holding the surgical suture;

second guide means, connected to said upper outer surface of said handle at a location longitudinally displaced from and distal to said first guide means, for releasably, guidingly, holding the surgical suture; and wherein said bore terminates at an opening in said upper outer surface of said handle intermediate the locations of said first and second guide means.

3. A suture passer comprising:

a longitudinally extending hollow cannula having a central passage slidingly receivable of a surgical suture;

a manually graspable handle connected to said hollow cannula for manipulation thereof, said handle having an upper outer surface;

first guide means comprising a single turn open loop, having a first axis of rotation of said loop, said first guide means being connected to said upper outer surface of said handle at a location proximate a proximal end of said handle, for releasably, guidingly, holding the surgical suture; and second guide means comprising a one and one-half turn open loop, having a second axis of rotation of said loop, said second guide means being connected to said upper outer surface of said handle at a location longitudinally displaced from and distal to said first guide means, for releasably, guidingly, holding the surgical suture.

4. The suture passer according to claim 3, wherein said first axis of rotation and said second axis of rotation are parallel to one another.

5. The suture passer according to claim 4, wherein said first axis of rotation is transverse to said longitudinally extending hollow cannula.

6. The suture passer according to claim 4, wherein said first axis of rotation is parallel to said longitudinally extending hollow cannula.

7. A suture passer comprising:

a longitudinally extending hollow cannula having a central passage slidingly receivable of a surgical suture;

a manually graspable handle connected to said hollow cannula for manipulation thereof, said handle having an upper outer surface;

first guide means comprising a single turn open loop lying in a first plane, said first plane disposed perpendicular to said longitudinally extending hollow cannula, said first guide means being connected to said upper outer surface of said handle at a location proximate a proximal end of said handle, for releasably, guidingly, holding the surgical suture; and second guide means comprising a plurality of bent fingers, each of said bent fingers lying in a plane, each of said planes containing said bent fingers being parallel to one another and perpendicular to said longitudinally extending hollow cannula, said second guide means being connected to said upper outer surface of said handle at a location longitudinally displaced from and distal to said first guide means, for releasably, guidingly holding the surgical suture.

8. The suture passer according to claim 7, wherein said plurality of bent fingers are alternately bent in opposite directions.

9. The suture passer according to claim 7, wherein said second guide means comprises three bent fingers.

10. A surgical repair kit comprising:

a suture passer comprising:

a longitudinally extending hollow cannula having a central passage slidingly receivable of a surgical suture;

a manually graspable handle connected to said hollow cannula for manipulation thereof, said handle having an upper outer surface;

first guide means, connected to said upper outer surface of said handle at a location proximate a proximal end of said handle, for releasably, guidingly, holding a surgical suture;

second guide means, connected to said upper outer surface of said handle at a location longitudinally displaced from and distal to said first guide means, for releasably, guidingly, holding a surgical suture;

at least two surgical needles of predetermined length; and at least one stylet for each surgical needle.

11. The surgical repair kit according to claim 10, wherein said surgical needles are epidural needles.

12. The surgical repair kit according to claim 11, wherein said epidural needles have a Huber tip.

13. The surgical repair kit according to claim 10, further comprising a third needle.

14. The surgical repair kit according to claim 13, wherein said third needle has a length greater than that of said surgical needles.

15. The surgical repair kit according to claim 10, wherein said suture passer comprises a metal cannula.

16. The surgical repair kit according to claim 15, further comprising a cannula bender for bending said metal cannula, said cannula bender comprising a base, a pair of upwardly stepped symmetrical bolsters positioned on top of said base allowing said cannula to be bent to the right or to the left, each step of each bolster having a predetermined radius of curvature wherein the radius of curvature of each step is smaller than the radius of curvature of the step immediately below.

17. The surgical repair kit, according to claim 16, wherein the height of each step is substantially greater than the diameter of the cannula.

18. The surgical repair kit according to claim 10, further comprising a parallel needle guide for guiding said needles, said parallel needle guide comprising at least three longitudinally extending, hollow, tube-shaped units longitudinally adhered to each other, in a plane, parallel to one another, each of said tube-shaped units slidingly receivable of a surgical needle therethrough.

* * * * *